(12) United States Patent
Madabhushi et al.

(10) Patent No.: US 11,798,179 B2
(45) Date of Patent: Oct. 24, 2023

(54) STRUCTURAL RECTAL ATLAS DEFORMATION FEATURES FOR CHARACTERIZING INTRA-WALL AND PERI-WALL CHEMORADIATION RESPONSE ON MAGNETIC RESONANCE IMAGING (MRI)

(71) Applicant: Case Western Reserve University, Cleveland, OH (US)

(72) Inventors: Anant Madabhushi, Shaker Heights, OH (US); Jacob Antunes, Cincinnati, OH (US); Zhouping Wei, Cleveland, OH (US); Pallavi Tiwari, Wexford, PA (US); Satish E. Viswanath, Pepper Pike, OH (US); Charlems Alvarez Jimenez, Bogotá (CO)

(73) Assignee: Case Western Reserve University, Cleveland, OH (US)

( * ) Notice: Subject to any disclaimer, the term of this patent is extended or adjusted under 35 U.S.C. 154(b) by 216 days.

(21) Appl. No.: 17/481,625

(22) Filed: Sep. 22, 2021

(65) Prior Publication Data
US 2022/0012902 A1 Jan. 13, 2022

Related U.S. Application Data

(63) Continuation-in-part of application No. 16/882,936, filed on May 26, 2020, now Pat. No. 11,158,051.
(Continued)

(51) Int. Cl.
*G06K 9/00* (2022.01)
*G06T 7/33* (2017.01)
(Continued)

(52) U.S. Cl.
CPC .............. *G06T 7/33* (2017.01); *G06T 7/38* (2017.01); *G16H 20/40* (2018.01); *G16H 50/70* (2018.01);
(Continued)

(58) Field of Classification Search
CPC ......... G06T 7/0014; G06T 2207/30096; G06T 2207/10088; G06T 7/337;
(Continued)

(56) References Cited

U.S. PATENT DOCUMENTS

| 2007/0019846 A1 | 1/2007 | Bullitt et al. |
| 2008/0123927 A1 | 5/2008 | Miga et al. |

(Continued)

OTHER PUBLICATIONS

Zeng "An image classification model based on transfer learning for ulcerative Proctitis," Jan. 21, 2021, Springer, Multimedia Systems (Year: 2021).
(Continued)

*Primary Examiner* — Alex Kok S Liew
(74) *Attorney, Agent, or Firm* — Eschweiler & Potashnik, LLC

(57) ABSTRACT

The present disclosure, in some embodiments, relates to a non-transitory computer-readable medium storing computer-executable instructions. The computer readable medium is configured to cause a processor to access an image volume of a rectum comprising a rectal tumor. A forward mapping is generated based on non-rigidly registering a healthy rectal atlas to the image volume. The forward mapping is inverted to generate an inverse mapping from the image volume to the healthy rectal atlas. Based on the inverse mapping, a plurality of deformation vectors, associated with a deformation within a rectal wall of the rectum, are determined. Magnitude based deformation features and orientation based deformation features are computed from the plurality of deformation vectors. One or more
(Continued)

of the magnitude based deformation features and one or more of the orientation based deformation features are utilized to determine a response of a patient to a chemoradiation treatment.

20 Claims, 12 Drawing Sheets

Related U.S. Application Data

(60) Provisional application No. 62/879,044, filed on Jul. 26, 2019.

(51) Int. Cl.
*G06T 7/38* (2017.01)
*G16H 20/40* (2018.01)
*G16H 50/70* (2018.01)

(52) U.S. Cl.
CPC .............. *G06T 2207/10088* (2013.01); *G06T 2207/30096* (2013.01)

(58) Field of Classification Search
CPC ............ G06T 2207/30004; G06T 7/38; G06T 7/0016; G06T 2207/30036; G06T 2207/30088; G06T 3/0081; G06T 7/11; G06T 7/12; G06T 7/149; G06T 7/30; G06T 7/33; G06T 2207/10072; G06T 2207/10136; G06T 2207/20081; G06T 2207/30081; G06T 3/0068; G06T 2207/10132; G06T 2207/20048; G06T 7/40; G06T 2200/24; G06T 2207/20084; G06T 2207/20124; G06T 2207/30028
See application file for complete search history.

(56) References Cited

U.S. PATENT DOCUMENTS

| | | | | |
|---|---|---|---|---|
| 2014/0309477 | A1* | 10/2014 | Finkelstein | A61N 5/1039 600/1 |
| 2018/0025489 | A1* | 1/2018 | Tiwari | G01R 33/5602 600/420 |
| 2018/0314906 | A1* | 11/2018 | Yang | G06V 10/462 |
| 2019/0070436 | A1* | 3/2019 | Willcut | A61N 5/1039 |

OTHER PUBLICATIONS

Notice of Allowance dated Jul. 1, 2021 for U.S. Appl. No. 16/882,936.

* cited by examiner

```
110 ─ ACCESS PRE-TREATMENT IMAGE VOLUME OF RECTUM WITH
       RECTAL TUMOR

120 ─ GENERATE FORWARD MAPPING FROM HEALTHY RECTAL ATLAS
       TO PRE-TREATMENT IMAGE VOLUME

130 ─ INVERT FORWARD MAPPING TO GENERATE INVERSE MAPPING
       FROM IMAGE VOLUME TO ATLAS

140 ─ DETERMINE DEFORMATION MAGNITUDE FOR VOXELS OF INTRA-
       AND/OR PERI-WALL REGION FROM INVERSE MAPPING

150 ─ COMPUTE STRUCTURAL DEFORMATION FEATURE(S) FROM
       DEFORMATION MAGNITUDES OF VOXELS

160 ─ OPTIONALLY COMPUTE TEXTURE FEATURE(S) FOR INTRA- AND/
       OR PERI-WALL REGION

170 ─ PREDICT RESPONSE TO CHEMORADIATION TREATMENT BASED
       ON STRUCTURAL DEFORMATION AND/OR TEXTURE FEATURES
       VIA CLASSIFIER
```

STRUCTURAL RECTAL ATLAS DEFORMATION FEATURES FOR CHARACTERIZING INTRA-WALL AND PERI-WALL CHEMORADIATION RESPONSE ON MAGNETIC RESONANCE IMAGING (MRI)

CROSS REFERENCE TO RELATED APPLICATIONS

This application is a Continuation-in-Part of U.S. application Ser. No. 16/882,936, filed on May 26, 2020, which claims the benefit of U.S. Provisional Application No. 62/879,044, filed on Jul. 26, 2019. The contents of the above-referenced patent applications are hereby incorporated by reference in their entirety.

FEDERAL FUNDING NOTICE

This invention was made with government support under the grants CA199374, CA202752, CA208236, CA216579, CA220581, CA216935, RR012463, EB750912, EY022947, DK097948, and EB007509 awarded by the National Institutes of Health; grants W8IXWH-15-1-0558, W8IXWH-16-1-0329, W8IXWH-18-1-0404, and W81XWH-18-1-0440 awarded by the Department of Defense; and grant IBX004121A awarded by the United States Department of Veterans Affairs. The government has certain rights in the invention.

BACKGROUND

The advent of radiomics has demonstrated great success for predicting and evaluating treatment response via imaging in different cancers. Radiomic approaches have typically extracted morphologic texture or shape descriptors of the tumor region, which have been related to underlying pathologic or molecular heterogeneity that drive therapy response. As an example, prediction of response to chemoradiation in rectal cancers via pre- or post-treatment MRI has been limited to using morphologic radiomic descriptors for image appearance alone. Unlike deep learning approaches (which are data-driven solutions to lesion segmentation, localization, or detection), radiomics also leverages "handcrafted" descriptors to quantify specific imaging characteristics both within and around the tumor. For instance, new classes of features that quantify tissue deformations or surface distensions on imaging have been linked to aggressive tumor growth as well as tumor recurrence, based on available reference atlas representations in solid organs such as the brain or the prostate.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 1 illustrates a flow diagram of an example method/set of operations that can be performed by one or more processors to predict a response to chemoradiation treatment based on structural deformation features and/or texture features of a pre-treatment imaging volume of a rectum with rectal cancer, according to various aspects discussed herein.

DETAILED DESCRIPTION

Figure 2:
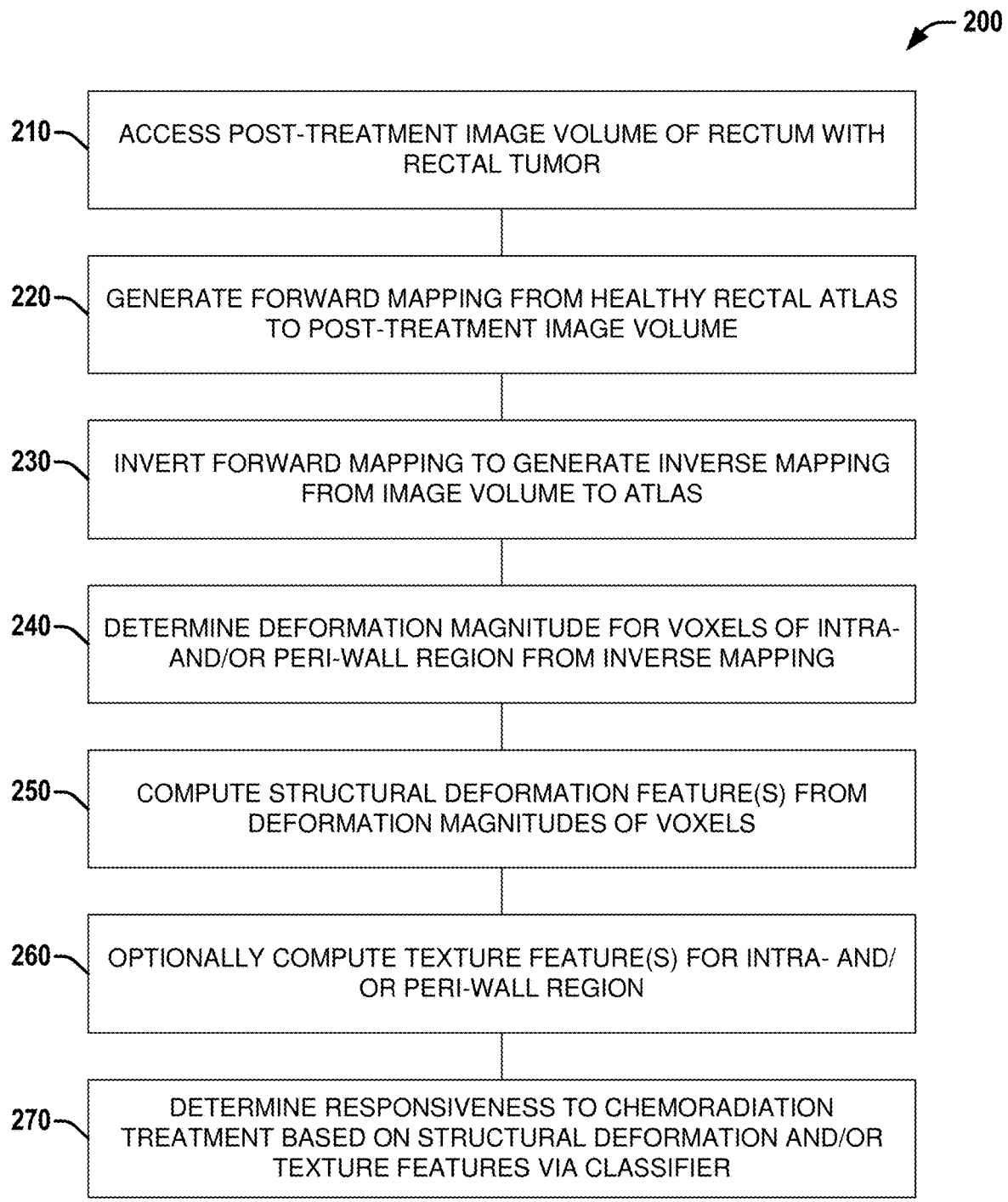
FIG. 2 illustrates a flow diagram of an example method/set of operations that can be performed by one or more processors to determine responsiveness to chemoradiation treatment based on structural deformation features and/or texture features of a post-treatment imaging volume of a rectum with rectal cancer, according to various aspects discussed herein.

Various embodiments discussed herein can comprise techniques that can facilitate determination of response of rectal cancer to chemoradiation treatment based on pre-treatment medical imaging (e.g., MRI (Magnetic Resonance Imaging)) and/or post-treatment medical imaging of a patient. Based on mapping of a healthy rectal atlas to the medical imaging of the patient, one or more structural features can be determined. Based on a set of features comprising the one or more structural features and/or one or more texture features, a determination can be made regarding chemoradiation response for the patient via a classifier trained on the set of features.

Techniques discussed herein can be employed by various embodiments to one or more of: (a) predict a response to chemoradiation treatment from pre-treatment medical imaging of rectal cancer, (b) determine whether rectal cancer is likely to regress following chemoradiation treatment based on post-treatment medical imaging of rectal cancer, or (c) train a classifier to facilitate one or more of (a) or (b). The techniques discussed herein comprise techniques that facilitate: (1) construction of a healthy structural rectal atlas; (2) computing structural deformations of medical imaging of a rectal cancer patient with respect to the atlas; (3) extracting structural and/or texture features from subregions within the rectal wall and/or peri-rectal environment from the imaging of the patient; (4) training classifier(s) to predict response to chemoradiation treatment and/or determine tumor regression following chemoradiation treatment; (5) predicting response or non-response to chemoradiation treatment from baseline medical imaging; and/or (6) identifying good or poor responders after chemoradiation treatment from post-therapy medical imaging. Each of these techniques are discussed in greater detail below, along with example application of specific techniques in connection with a use case, although the specific techniques employed can vary, depending on the embodiment.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Referring to FIG. 1, illustrated is a flow diagram of an example method/set of operations 100 that can be performed by one or more processors to predict a response to chemoradiation treatment based on structural deformation features and/or texture features of a pre-treatment imaging volume of a rectum with rectal cancer, according to various aspects discussed herein. Processor(s) can include any combination of general-purpose processors and dedicated processors (e.g., graphics processors, application processors, etc.). The one or more processors can be coupled with and/or can include memory or storage and can be configured to execute instructions stored in the memory or storage to enable various apparatus, applications, or operating systems to perform the operations. The memory or storage devices may include main memory, disk storage, or any suitable combination thereof. The memory or storage devices can comprise—but is not limited to—any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 can comprise, at 110, accessing an image volume of the rectum of a patient with rectal cancer, wherein the image volume was obtained prior to chemoradiation treatment. In various embodiments and in the example use case discussed below, the image volume can comprise a Magnetic Resonance Imaging (MRI) image volume. In other embodiments, other medical imaging techniques can be employed to obtain the image volume. The image volume can be obtained via a system and/or apparatus implementing the set of operations 100, or can be obtained from a separate medical imaging system. Additionally, the image volume can be accessed contemporaneously with or at any point prior to performing the set of operations 100.

The set of operations 100 can further comprise, at 120, generating a forward mapping from a healthy rectal atlas (e.g., generated according to techniques discussed herein, etc.) to the image volume via techniques discussed herein (e.g., via non-rigid registration, etc.).

The set of operations 100 can further comprise, at 130, inverting the forward mapping to generate an inverse mapping from the image volume to the healthy rectal atlas.

The set of operations 100 can further comprise, at 140, determining a deformation magnitude relative to the healthy rectal atlas for each voxel of an intra-wall and/or peri-wall region of a region of interest based on the inverse mapping (e.g., in one or more sites N consecutive slices associated with a tumor, etc.).

The set of operations 100 can further comprise, at 150, computing one or more structural deformation features from the deformation magnitudes of intra-wall and/or peri-wall voxels. The one or more structural deformation features can comprise statistical measures of the intra-wall voxels and/or statistical measures of the peri-wall voxels.

The set of operations 100 can further comprise, at 160, optionally computing one or more texture features for the intra-wall region and/or one or more texture features for the peri-wall region.

The set of operations 100 can further comprise, at 170, predicting a response to chemoradiation treatment based on the one or more structural deformation features and/or the one or more texture features via a classifier trained according to aspects discussed herein.

Additionally or alternatively, set of operations 100 can comprise one or more other actions discussed herein in connection with predicting a response to chemoradiation treatment based on pre-treatment medical imaging.

Referring to FIG. 2, illustrated is a flow diagram of an example method/set of operations 200 that can be performed by one or more processors to determine responsiveness to chemoradiation treatment based on structural deformation features and/or texture features of a post-treatment imaging volume of a rectum with rectal cancer, according to various aspects discussed herein.

The set of operations 200 can comprise, at 210, accessing an image volume of the rectum of a patient with rectal cancer, wherein the image volume was obtained after chemoradiation treatment. In various embodiments and in the example use case discussed below, the image volume can comprise a MRI image volume. In other embodiments, other medical imaging techniques can be employed to obtain the image volume. The image volume can be obtained via a system and/or apparatus implementing the set of operations 200, or can be obtained from a separate medical imaging system. Additionally, the image volume can be accessed contemporaneously with or at any point prior to performing the set of operations 200.

The set of operations 200 can further comprise, at 220, generating a forward mapping from a healthy rectal atlas (e.g., generated according to techniques discussed herein, etc.) to the image volume via techniques discussed herein (e.g., via non-rigid registration, etc.).

The set of operations 200 can further comprise, at 230, inverting the forward mapping to generate an inverse mapping from the image volume to the healthy rectal atlas.

The set of operations 200 can further comprise, at 240, determining a deformation magnitude relative to the healthy rectal atlas for each voxel of an intra-wall and/or peri-wall region of a region of interest based on the inverse mapping (e.g., in one or more sites comprising N consecutive slices associated with a tumor, etc.).

The set of operations 200 can further comprise, at 250, computing one or more structural deformation features from the deformation magnitudes of intra-wall and/or peri-wall voxels. The one or more structural deformation features can comprise statistical measures of the intra-wall voxels and/or statistical measures of the peri-wall voxels.

The set of operations 200 can further comprise, at 260, optionally computing one or more texture features for the intra-wall region and/or one or more texture features for the peri-wall region.

The set of operations 200 can further comprise, at 270, determining responsiveness to chemoradiation treatment (e.g., classification as a good responder or non-responder, etc.) based on the one or more structural deformation features and/or the one or more texture features via a classifier trained according to aspects discussed herein.

Additionally or alternatively, set of operations 200 can comprise one or more other actions discussed herein in connection with determining responsiveness to chemoradiation treatment based on post-treatment medical imaging.

Figure 3:
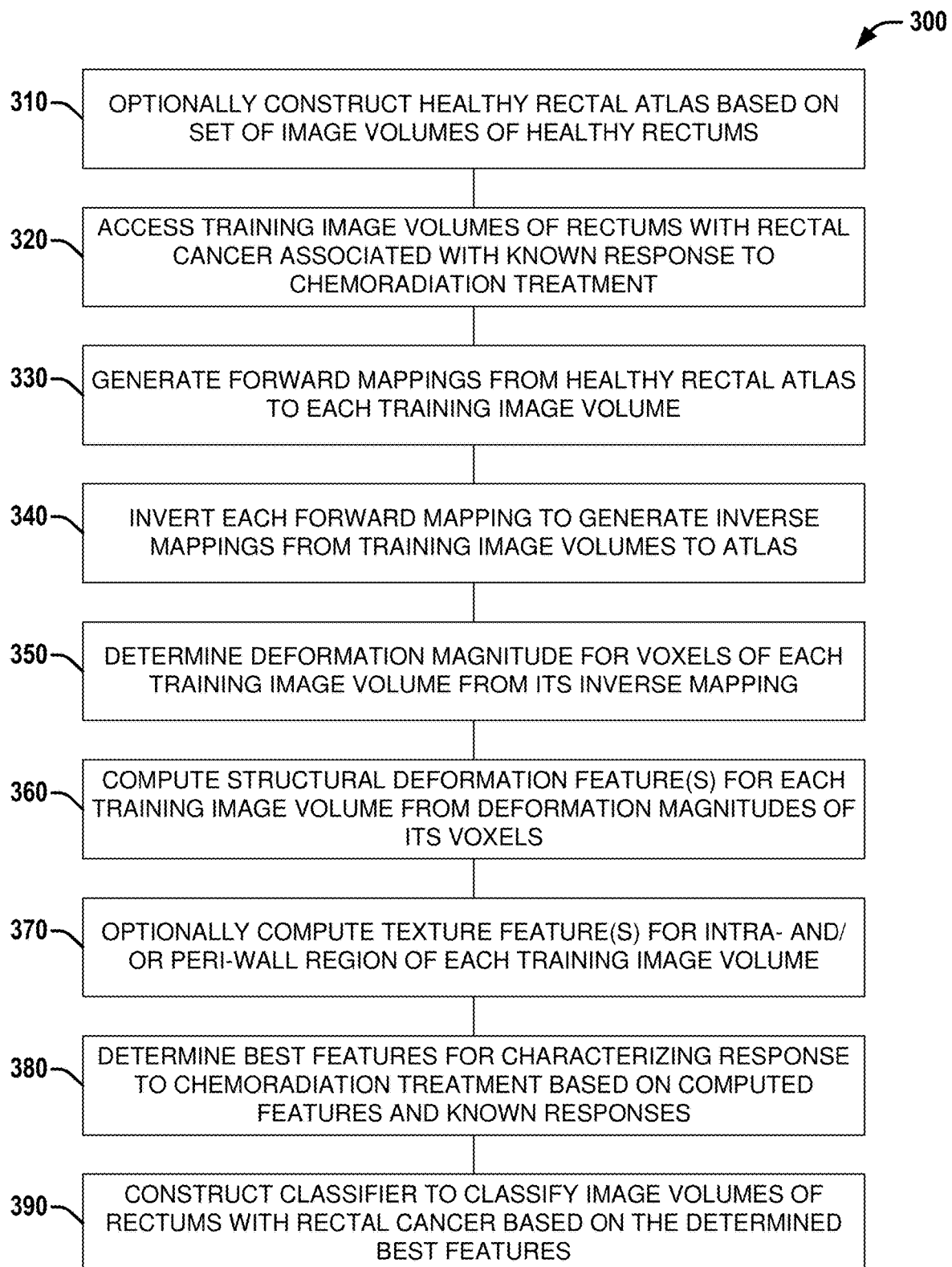
FIG. 3 illustrates a flow diagram of an example method/set of operations that can be performed by one or more processors to determine responsiveness to chemoradiation treatment based on structural deformation features and/or texture features of a post-treatment imaging volume of a rectum with rectal cancer, according to various aspects discussed herein.

Referring to FIG. 3, illustrated is a flow diagram of an example method/set of operations 300 that can be performed by one or more processors to train a Machine Learning (ML) classifier to predict or determine responsiveness of rectal cancer to chemoradiation treatment based on structural deformation and/or texture features of pre- or post-treatment medical imaging, according to various aspects discussed herein.

The set of operations 300 can comprise, at 310, optionally constructing a healthy rectal atlas based on a set of image volumes of healthy rectums, according to techniques discussed herein. In other embodiments, a previously constructed healthy rectal atlas can be employed by the set of operations 300. In various embodiments and in the example use case discussed below, image volumes employed by set of operations 300 can comprise MRI image volumes. In other embodiments, other medical imaging techniques can be employed to obtain the image volumes. The image volumes can be obtained via a system and/or apparatus implementing the set of operations 300, or can be obtained from a separate medical imaging system. Additionally, the image volumes can be accessed contemporaneously with or at any point prior to performing the set of operations 300.

The set of operations 300 can further comprise, at 320, accessing a training set of image volumes of rectums of patients with rectal cancer. Each of the image volumes in the training set can be associated with a known response to chemoradiation treatment by the patient of that image volume. In some embodiments, each image volume of the training set can comprise baseline imaging taken prior to chemoradiation treatment, while in other embodiments, each image volume of the training set can comprise imaging taken after chemoradiation treatment.

The set of operations 300 can further comprise, at 330, generating an associated forward mapping from a healthy rectal atlas (e.g., generated according to techniques discussed herein, etc.) to each image volume of the training set via techniques discussed herein (e.g., via non-rigid registration, etc.).

The set of operations 300 can further comprise, at 340, inverting the forward mapping for each image volume of the training set of the training set to generate an inverse mapping from that image volume to the healthy rectal atlas.

The set of operations 300 can further comprise, at 350, determining a deformation magnitude relative to the healthy rectal atlas for each voxel of an intra-wall and/or peri-wall region of a region of interest of each image volume of the training set based on the inverse mapping for that image volume (e.g., in one or more sites of N consecutive slices associated with a tumor, etc.).

The set of operations 300 can further comprise, at 360, computing one or more structural deformation features for each image volume of the training set from the deformation magnitudes of intra-wall and/or peri-wall voxels of that image volume. The one or more structural deformation features can comprise statistical measures of the intra-wall voxels and/or statistical measures of the peri-wall voxels.

The set of operations 300 can further comprise, at 370, for each image volume of the training set, optionally computing one or more texture features for the intra-wall region of that image volume and/or one or more texture features for the peri-wall region of that image volume.

The set of operations 300 can further comprise, at 380, determining one or more best features for characterizing response to chemoradiation treatment based on the known responses to chemoradiation treatment for the patients, the computed structural deformation features for each image volume of the training set, and optionally the computed texture features for each image volume of the training set. Feature selection can be as discussed in connection with the example use case, or can employ other feature selection algorithms.

The set of operations 300 can further comprise, at 390, constructing a machine learning (ML) classifier trained to classify image volumes as responsive or non-responsive to chemoradiation treatment based on values determined for that image volume for the best features determined at 380.

Additionally or alternatively, set of operations 300 can comprise one or more other actions discussed herein in connection with training a classifier to predict or determine responsiveness to chemoradiation treatment based on post-treatment medical imaging.

Additional aspects and embodiments are discussed below in connection with the following example use case.

Example Use Case: Structural Rectal Atlas Deformation Features for Characterizing Intra- and Peri-Wall Chemoradiation Response on MRI The following discussion provides example embodiments in connection with an example use case involving determination of chemoradiation response in rectal cancer based on pre-treatment MRI or based on post-treatment MRI via techniques discussed herein. These techniques comprise: (1) construction of a healthy structural rectal atlas; (2) computing structural deformations of medical imaging of a rectal cancer patient with respect to the atlas; (3) extracting structural and/or texture features from subregions within the rectal wall and/or peri-rectal environment from the imaging of the patient; (4) training classifier(s) to predict response to chemoradiation treatment and/or determine tumor regression following chemoradiation treatment; (5) predicting response or non-response to chemoradiation treatment from baseline medical imaging; or (6) identifying good or poor responders after chemoradiation treatment from post-therapy medical imaging. Each of techniques (1)-(6) are described in greater detail below. Although specific details and aspects were employed for the example use case as a specific concrete embodiment, it is to be appreciated that in various embodiments, these details and aspects can vary.

A. Overview

Radiomic features which quantify morphologic texture and shape of tumor regions on imaging have found wide success in characterizing treatment response in vivo. A more detailed interrogation of intra- and peri-tumoral regions for response-related cues could be achieved by capturing subtle structural deformations that occur due to tumor shrinkage or growth. The example use case employed a set of Structural Rectal Atlas Deformation features to quantify tumor-related deformations in rectal cancers via a cohort of 139 patient MRIs. In flexible non-rigid organs such as the rectum, inter-patient differences complicate evaluation of tumor-related deformations that may occur within the rectal wall or in the peri-rectal environment; necessitating construction of a canonical rectal imaging atlas. Using 63 pelvic MRIs where healthy rectums could be clearly visualized, the example use case employed the first structural atlas built for the healthy rectal wall. This atlas was used to compute structural deformations within and around locations in the rectal wall of patients where tumor was present, resulting in intra- and peri-wall Structural Rectal Atlas Deformation descriptors. The example use case evaluated the efficacy of these Structural Rectal Atlas Deformation features in 2 different tasks: (a) predicting which rectal tumors will or will not respond to therapy via baseline MRIs (n=42), and (b) identifying which rectal tumors were exhibiting regression on post-chemoradiation MRIs (n=34). Using a linear discriminant analysis classifier in a three-fold cross-validation scheme, it was found that intra-wall deformations were significantly lower for responders to chemoradiation; both on baseline MRIs (with AUC (Area Under ROC (Receiver Operating Characteristic) Curve)=0.73±0.05) as well as on post-therapy MRIs (AUC=0.87±0.03). By comparison, radiomic texture features for both intra- and peri-wall locations yielded significantly worse classification performance in both tasks.

As discussed above, for solid organs such as the brain or prostate, new classes of features that quantify tissue deformations or surface distensions on imaging have been linked to aggressive tumor growth and tumor recurrence. Quantifying such structural changes in more flexible organs such as the rectum requires construction of a healthy rectal wall atlas (e.g., the rectal anatomy without a tumor). In connection with the example use case, it was hypothesized that constructing a healthy rectal atlas could then allow for a unique quantification of disease-specific structural changes in the rectal environment (wall/tumor, peri-wall/tumor) that may be closely related to tumor response to therapy. The hypothesis was tested via the following aspects of the example use case (discussed in greater detail below): (1) Development of the first structural atlas representation for healthy rectal wall anatomy, via a multi-stage registration scheme using pelvic MRIs (from other cancers) where normal rectums are visible and (2) The first attempt at relating subtle structural deformations occurring within and around rectal wall regions to chemoradiation-related tumor growth or shrinkage in vivo.

The Structural Rectal Atlas Deformation features discussed herein were evaluated in the context of two distinct clinical problems in rectal cancer: (a) prediction of pathologic non-responders to chemoradiation via baseline treatment-naïve MRI, and (b) assessment of pathologic responders on post-chemoradiation MRI. Together, these two problems represent the major clinical challenges facing personalization of patient management in rectal cancers.

B. Methodology

Quantifying structural deformations within and around the rectum involves the following 3 acts: (i) building a structural atlas for normal rectal wall anatomy on imaging, (ii) computing structural deformations of the rectal wall in patients with tumors with respect to this atlas, and (iii) extracting tumor-related structural deformation descriptors within the rectal wall and peri-rectal environment.

Figure 4:
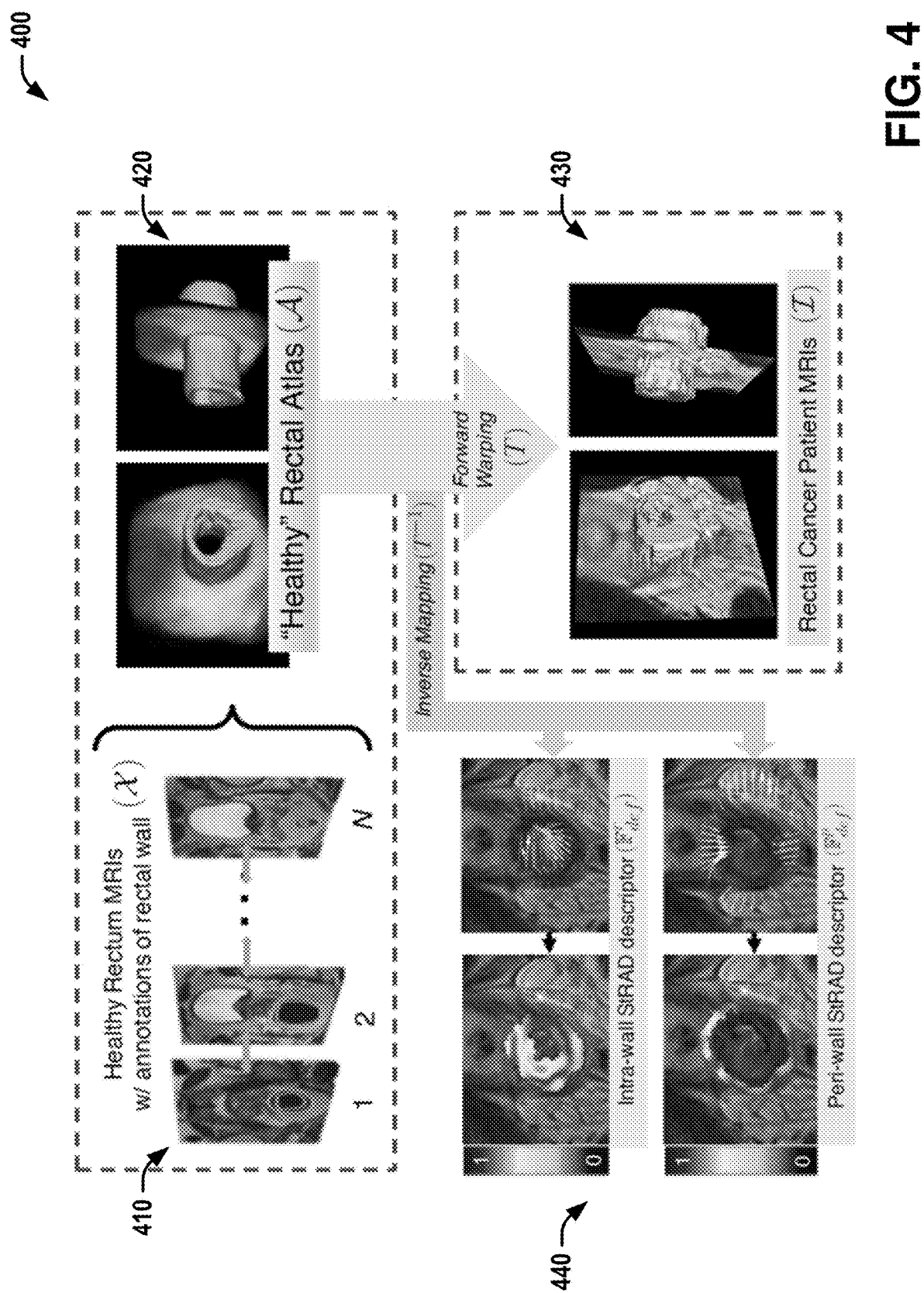
FIG. 4 illustrates a series of example diagrams showing actions involved in extracting Structural Rectal Atlas Deformation features from a patient MRI, according to various aspects discussed herein.

Referring to FIG. 4, illustrated is a series of example diagrams 400 showing actions involved in extracting Structural Rectal Atlas Deformation features from a patient MRI, according to various aspects discussed herein. At 410, a set of healthy rectum MRI images with annotated rectal walls (e.g., via expert annotation, etc) can be obtained. At 420, a healthy rectal atlas can be constructed from the healthy rectum MRI images according to techniques discussed herein. At 430, a forward mapping from the atlas to the MRI of a rectal cancer patient can be determined. At 440, based on the forward mapping, an inverse mapping from the MRI of the patient to the atlas can be determined, based on which deformations within and around the rectal wall with respect to the atlas can be determined. At 450, based on the determined deformations, structural deformation features can be extracted for an intra-wall and/or peri-wall region of the MRI of the patient.

Construction of Structural Rectal Atlas

A set of N MRI scenes depicting the healthy rectum was utilized, and denoted X=(C, f), where C is a 3-dimensional spatial grid and f(c) represents the MRI intensity at each voxel $c \in C$. The primary anatomic region defined within this MRI scene is the healthy rectal wall, denoted $X^r = (C, f^r)$, where $f^r(c)=1$ within the rectal wall and zero in the rest of the scene. $X^r$ can be identified and annotated by experts on all X, and is depicted in the images of 410 in FIG. 4.

The final output of this construction is the healthy rectal wall atlas, denoted $A=(C,g^r)$, with $g^r(c)\in[0,1]$ defined as the frequency of a particular location $c \in C$ where $f^r(c)=1$ (e.g., corresponding to rectal wall); across N different input subject scenes. These N different subject scenes were aligned to a registration template for projection into a canonical space to construct A, via the following three transformations.

The first transformation can be a simple transformation, $\tau_\rho$, that is used to map N different subject scenes X such that they are all centered and isotropically scaled in the X, Y, and Z axes. The resulting initial atlas, $A_\rho$, is therefore not dependent on selecting a specific subject as the template and can be constructed such that $A_\rho, =(C,g^r)$, where $$g^r(c) = \frac{1}{N}\sum_N f^r(c),$$

for every location $c \in C$, across all N studies after $\tau_\rho$ has been applied (e.g., $g^r(c)$ is the frequency of a location corresponding to the rectal wall).

In the second transformation, affine registration can be used to compute $\tau_\alpha$ for projecting all X onto $A_\rho$. The affinely transformed subject scenes can be used to construct $A_\alpha=(C, g^r)$ (based on re-computing $g^r(c)\forall c\in C$, across all N studies).

In the third transformation, deformable registration can be used to align X to $A_\alpha$. The final structural rectal atlas $A=(C, g^r)$, can be constructed based on re-computing $g^r(c)\forall c\in C$, across N deformed subject scenes.

Computing Structural Deformations with Respect to the Atlas

Given a rectal cancer patient MRI scene, denoted I, structural deformations in the rectal environment can be quantified with respect to the healthy atlas A. The rectal wall within the patient MRI scene is denoted $I^r$. First, A can be non-rigidly registered to I using a normalized mutual information-based similarity measure within a b-spline registration scheme. This non-rigid alignment can be formulated as $(I^r,I)=T(A)$, where T is the forward transformation of the composite voxel-wise deformation field (comprising affine and deformable components) that maps the rectal wall between the reference ($I^r$) and floating (A) volumes. This transformation can then be inverted to yield $T^{-1}$, which can be used to map I into the A space. This two-stage mapping process can be employed to compute structural deformations within I with respect to A at every $c\in C$, hypothesized to occur as a result of tumor-related growth or shrinkage of the rectal wall.

Extracting Structural Rectal Atlas Deformation (StRAD) Descriptors for Subregions within Rectal Wall and Peri-Rectal Environment Structural deformations can be quantified for each rectal cancer patient scene within $I^r$, as well for a peri-wall area denoted $I^p$. The latter was defined based on $I^r$ within each of the experiments later conducted. Once I is mapped to the A space, all voxel positions $(c_x,c_y,c_z)$ can be assumed to be displaced by $[\delta_x, \delta_y, \delta_z]$, to result in $(c_x',c_y',c_z')=(c_x,c_y,c_z)+[\delta_x, \delta_y, \delta_z]$. Based on this displacement vector, the deformation magnitude can be computed as $D(c)=\sqrt{(\delta_x)^2+(\delta_y)^2+(\delta_z)^2}$, for every $c\in C$. The descriptor $\mathbb{F}_{def}^r$ for intra-wall deformations can comprise first order statistics (e.g., mean, median, standard deviation, skewness, and kurtosis) of $D(c)$ for all the voxels $c$ within the rectal wall $I^r$. Similarly, the peri-wall deformation descriptor $\mathbb{F}_{def}^p$ can be computed based on first-order statistics of the deformation magnitudes in $I^p$.

Experimental Design

Data Description

Healthy rectum cohort ($S_1$): A cohort of 63 patients who had been diagnosed with prostate cancer and had undergone an axial pelvic MRI scan were curated. These scans were selected based on having the healthy rectal wall being clearly visible, as no endorectal coil had been used.

Baseline RCa cohort ($S_2$): A cohort of 42 patients who had been diagnosed with rectal cancer were identified, all of whom had undergone axial 3 Tesla (T) T2w MR imaging before standard-of-care chemoradiation. A first objective of the example use case was to predict non-responders to chemoradiation using this baseline MRI scan. Pathologic tumor stage (T-stage, based on excised rectal specimens) was used as a marker of response, where ypT3-4 corresponded to extensive tumor being present in the specimen despite chemoradiation. Based on this pathologic classification, n=22 patients were identified as being non-responsive to chemoradiation (ypT3-4), and the remainder as good responders to chemoradiation (ypT0-2, n=20).

Post-therapy RCa cohort ($S_3$): A separate cohort of 34 RCa patients was curated, where patients had axial 3 T T2w MRIs available after undergoing standard-of-care chemoradiation but prior to excision surgery. In this cohort, the goal was to identify which patients exhibited marked tumor regression (based on pathologic T-stage) via the post-therapy MRI scan. With ypT0-2 indicating minimal or dying tumor within the rectal wall after chemoradiation, n=17 patients were assessed as being good responders and the remaining n=17 were classified as exhibiting minimal or no response to chemoradiation (ypT3-4).

Implementation Details

For all 139 MRI scans in cohorts $S_{1-3}$, the entire length of the visible rectal wall from the anus to the peritoneal reflection was annotated by an expert radiologist. For the 76 RCa cases in $S_2$ and $S_3$, the slices most suspicious for tumor presence were also identified by the radiologist (using anatomic information from pathology reports). The healthy atlas A was constructed using N=63 MRI pelvic scans in $S_1$ using the approach discussed herein. Evaluation of the atlas in terms of overlap in annotated rectal wall as well as internal lumen regions (across all patients in $S_1$ after deformable mapping) yielded a Dice similarity coefficient of 0.87, indicating A was a relatively accurate representation.

Deformation fields for the remaining 79 RCa scans in $S_2$ and $S_3$ (with respect to A) were then computed to yield intra-wall and peri-wall StRAD descriptors, $\mathbb{F}_{def}^r$ and $\mathbb{F}_{def}^p$ respectively (each a 5×1 vector in the example use case, although the size can vary in different embodiments). The peri-wall region was empirically defined as an 8 pixel band along the outer wall boundary for $S_2$ and $S_3$. All registration steps were implemented using elastix, with a grid spacing of 9×9×9 (in the example use case, although the size can vary in different embodiments) when computing b-spline deformations. Radiomic texture features were also extracted to characterize the appearance of intra- and peri-wall areas on all 79 RCa scans, yielding $\mathbb{F}_{tex}^r$ and $\mathbb{F}_{tex}^p$ (each a 825×1 vector in the example use case, although the size can vary in different embodiments). Both deformation and texture features were extracted from 3 consecutive slices (the number of slices can vary depending on the embodiment) comprising the largest wall area suspicious for tumor, assuming that this region was most likely to exhibit signatures related to tumor growth or shrinkage on MRI.

Separate experiments were conducted using each of $S_2$ and $S_3$ in a cross-validation setting, with the goal of distinguishing between the 2 patient groups in each cohort. Following feature extraction, minimum redundancy maximum relevance feature selection (mRMR) was used to identify the 3 most relevant features (although a different number could be employed in various embodiments) within each of $\mathbb{F}_{def}^r$, $\mathbb{F}_{def}^p$, $\mathbb{F}_{tex}^r$, and $\mathbb{F}_{tex}^p$. The most relevant set of features from each vector was then evaluated via a Linear Discriminant Analysis (LDA) classifier (although other machine learning classifiers can be employed in various embodiments, e.g., Quadratic Discriminant Analysis (QDA), Support Vector Machine (SVM), Random Forest (RF), etc.). A total of 50 iterations (in various embodiments, the number of iterations can vary) of a three-fold (e.g., with one fold held-out for testing), patient-stratified, cross-validation scheme were utilized to ensure robustness of feature selection and classifier evaluation steps; with Receiver Operating Characteristic (ROC) analysis for evaluation. These steps were repeated for each of $S_2$ and $S_3$, and the area under the ROC curve (AUC) across all cross-validation runs was used to compare each of $\mathbb{F}_{def}^r$, $\mathbb{F}_{def}^p$, $\mathbb{F}_{tex}^r$, and $\mathbb{F}_{tex}^p$ (via Wilcoxon ranksum testing, although other feature selecting algorithms can be employed in various embodiments) to determine which feature set was most relevant for treatment response characterization.

Results and Discussion

Experiment 1: Predicting Non-Responders to Chemoradiation Via Baseline MRIs

Figure 5:
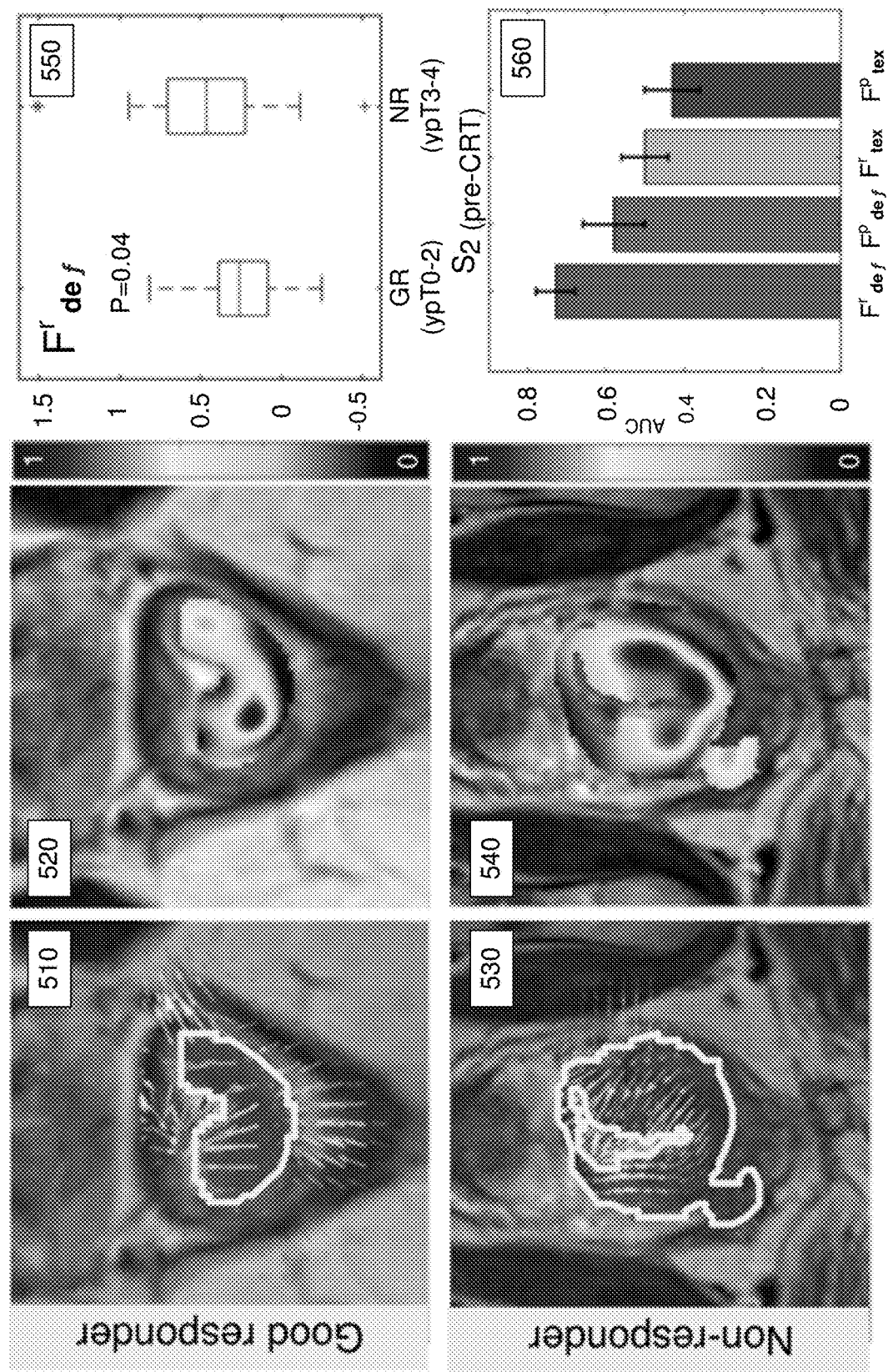
FIG. 5 illustrates example diagrams and graphs associated with predicting non-responders to chemoradiation via baseline MRIs in the example use case, according to various aspects discussed herein.

The most relevant StRAD descriptors identified in experimental evaluation of $S_2$ were the skewness and standard deviation of intra-wall deformation magnitudes. Referring to FIG. 5, illustrated are example diagrams and graphs associated with predicting non-responders to chemoradiation via baseline MRIs in the example use case, according to various aspects discussed herein. At 510 and 530 are representative baseline T2w MRI scans from $S_2$ for two different patients showing the deformation field as colored arrows within the rectal wall (annotated in 510 and 530). At 520 and 540, the corresponding intra-wall deformation magnitudes for 510 and 530, respectively, are visualized as a heatmap, where higher values/shades correspond to higher D(c). At 550, boxplots of skewness in deformation magnitudes reveal intra-wall deformations in non-responders to chemoradiation are positively skewed (e.g., having larger magnitudes in NR patients, ypT3-4) compared to good responders (GR). At 560, a bar plot of AUC values is presented for different feature descriptors, showing that $\mathbb{F}_{def}^r$ resulted in a significantly higher performance than $\mathbb{F}_{def}^p$, $\mathbb{F}_{tex}^r$, and $\mathbb{F}_{tex}^p$. The results of the first experiment indicate that non-responders to chemoradiation may be associated with significantly higher structural deformations within the rectal wall on baseline MRI scans (as seen at 550, showing positive skew associated with non-responders), when compared to the healthy rectal atlas. This resonates with previous findings where it has been reported that smaller rectal tumors tend to respond favorably to chemoradiation, which would result in their being associated with less pronounced wall deformations (with reference to a healthy atlas). Further, the intra-wall StRAD descriptor ($\mathbb{F}_{def}^r$) also yielded the best overall AUC in this classification task ($\mathbb{F}_{def}^r$ is shown in the leftmost bar of 560, with a AUC of 0.73±0.05). This was significantly higher (p<0.001) than the AUCs for each of $\mathbb{F}_{def}^p$, $\mathbb{F}_{tex}^r$, and $\mathbb{F}_{tex}^p$.

Figure 6:
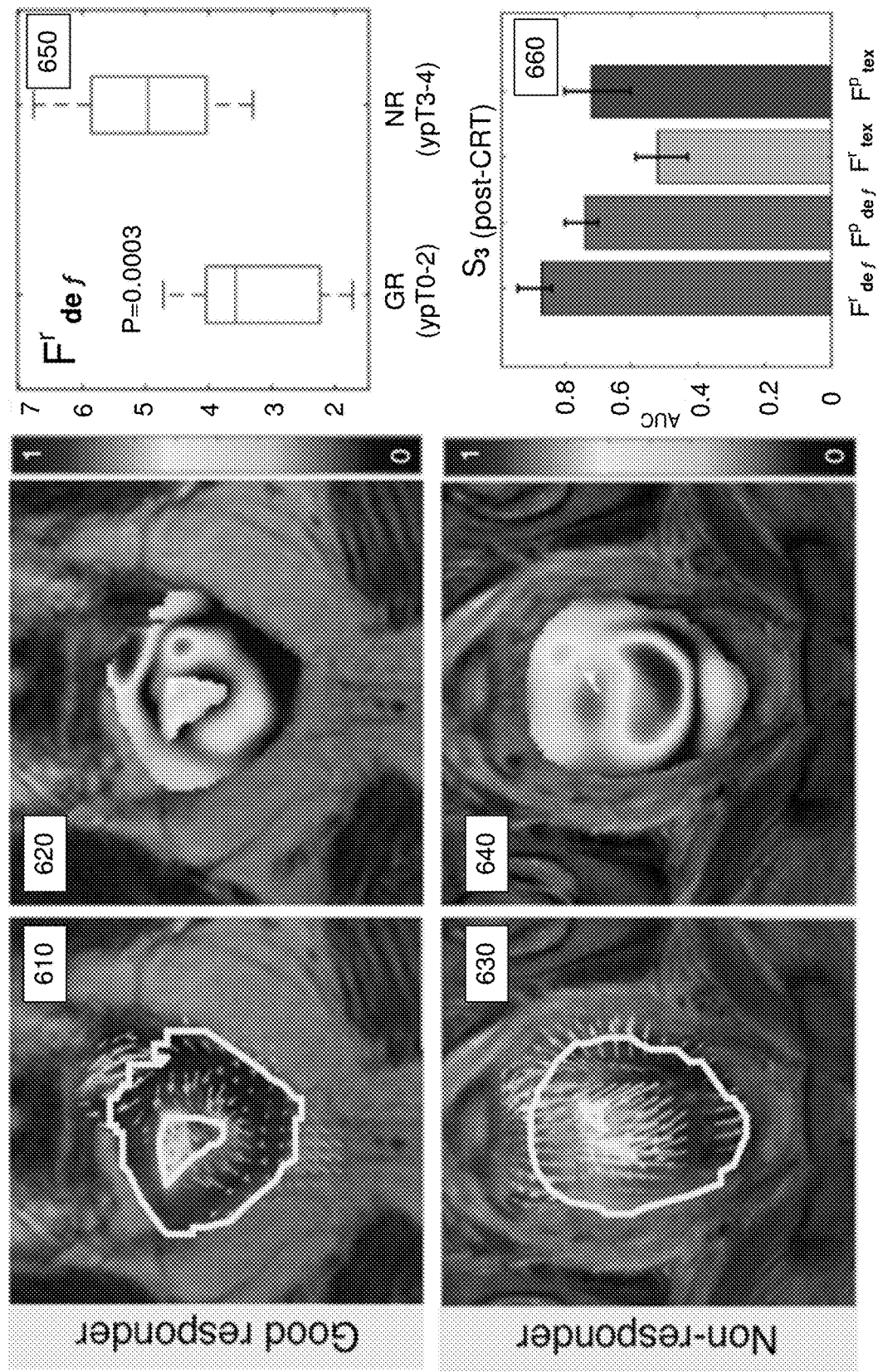
FIG. 6 illustrates example diagrams and graphs associated with identifying good responders after chemoradiation via post-therapy MRIs in the example use case, according to various aspects discussed herein.

Experiment 2: Identifying Good Responders after Chemoradiation Via Post-Therapy MRIs In $S_3$, the median and standard deviation of the intra-wall deformation magnitude were identified as the most relevant StRAD descriptors. Referring to FIG. 6, illustrated are example diagrams and graphs associated with identifying good responders after chemoradiation via post-therapy MRIs in the example use case, according to various aspects discussed herein. At 610 and 630 are representative post-therapy T2w MRI scans from $S_3$ for two different patients showing the deformation field visualized as arrows within the annotated outline of the rectal wall. At 620 and 640 are the corresponding intra-wall deformation magnitudes for the patients of 610 and 630, respectively, visualized as heatmaps, where higher values/shades correspond to higher D(c). At 650, boxplots of standard deviation of deformation magnitudes within the rectal wall reveal significantly less variable deformations associated with good responders to chemoradiation (GR, ypT0-2) compared to non-responders (NR). At 660, a bar plot of AUC values is presented for different feature descriptors, showing that $\mathbb{F}_{def}^r$ resulted in a significantly higher performance than $\mathbb{F}_{def}^p$, $\mathbb{F}_{tex}^r$, and $\mathbb{F}_{tex}^p$. As can be seen from FIG. 6, good responders are associated with significantly lower and less variable structural intra-wall deformations. As non-responders (e.g., ypT3-4) are likely to have more tumor extent outside the rectal wall despite chemoradiation, this would be reflected in the rectal wall being more deformed with respect to the healthy rectal atlas. The intra-wall StRAD descriptor ($\mathbb{F}_{def}^r$) significantly outperformed all of $\mathbb{F}_{def}^p$, $\mathbb{F}_{tex}^r$, and $\mathbb{F}_{tex}^p$ in terms of AUC values for this classification task, with an AUC of 0.87±0:03, p<0.001, as shown at 660.

Conclusion

The example use case presented a novel suite of STructural Rectal Atlas Deformation (StRAD) features for characterizing intra- and peri-wall response to chemoradiation on rectal MRIs. The example use case involved construction of the first reference healthy rectal wall atlas, which was applied to compute tumor-related deformations on baseline and post-chemoradiation MRIs, separately. StRAD features from within the rectal wall were found to be most effective for characterizing tumor treatment response on MRI, revealing that non-responder RCa patients in both pre- and post-therapy settings were associated with significantly higher and more variable intra-wall deformations; likely occurring as a result of more aggressive tumor growth. By contrast, morphologic texture features performed significantly worse both for predicting as well as evaluating response to therapy via MRI. The example use case provides specific examples of embodiments, but it is to be understood that other embodiments can vary from those of the example use case in one or more aspects, including as discussed herein. Various embodiments can employ StRAD features validated on a larger cohort of data, including multiple sites, as well as evaluation of parameter sensitivity. Additionally, various embodiments can integrate StRAD features with other morphologic descriptors and clinical variables to reliably predict and assess treatment response for rectal cancers in vivo.

ADDITIONAL EMBODIMENTS

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, 300, 400 or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein relate to training and/or employing classifiers to predict or determine a likelihood of response to chemoradiation treatment based on structural deformation and/or texture features associated with rectal cancer in a MRI image volume that are not perceivable by the human eye, and involve computation that cannot be practically performed in the human mind. As one example, machine learning and/or deep learning classifiers as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then be used and applied to create desired results more accurately, more consistently, and with greater reliability than existing approaches, thereby producing the technical effect of improving the performance of the machine, computer, or system with which embodiments are implemented.

Figure 7:
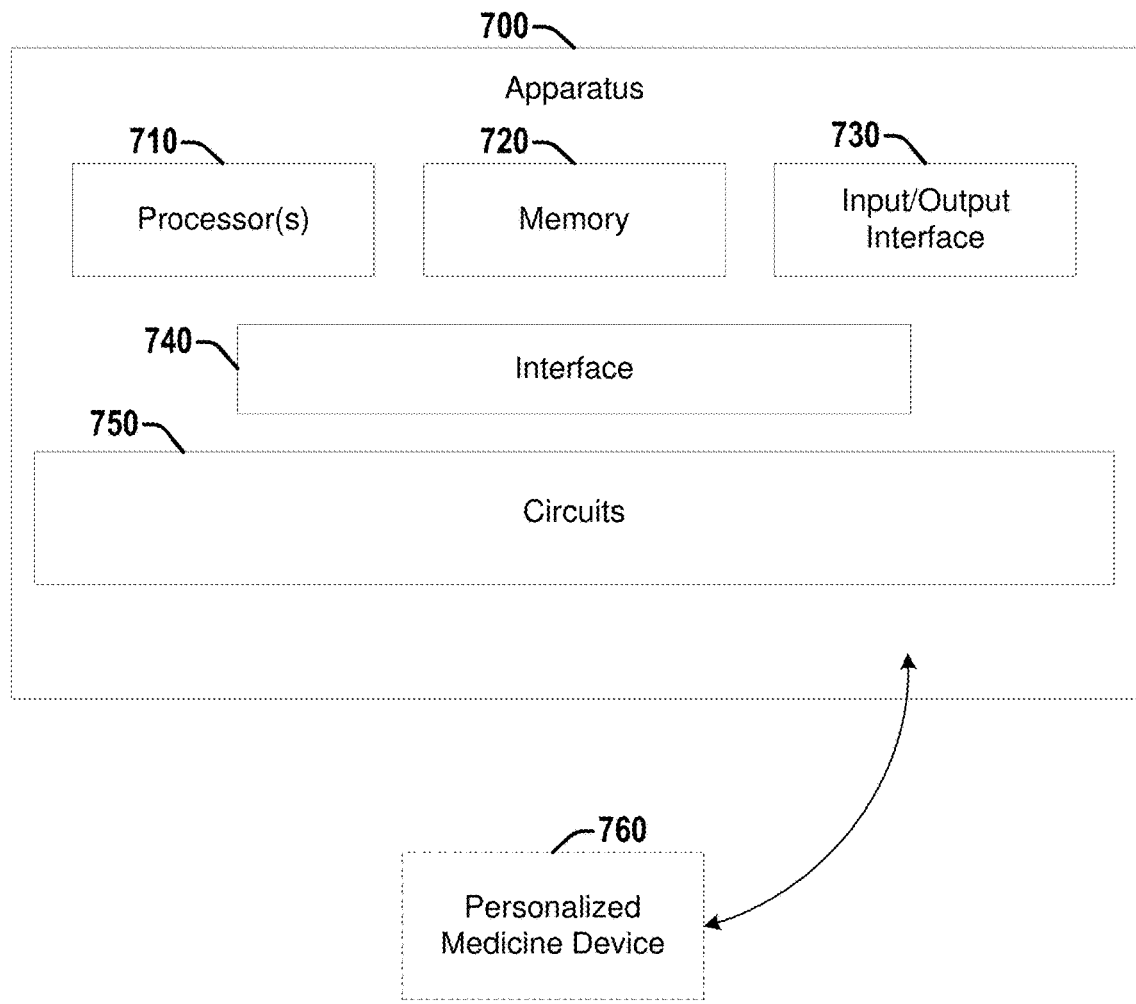
FIG. 7 illustrates a diagram of an example apparatus that can facilitate prediction and/or identification of responding and/or non-responding rectal cancer patients to chemoradiation treatment and/or training a machine learning (ML) classifier to perform such prediction and/or identification, according to various embodiments discussed herein.

Referring to FIG. 7, illustrated is a diagram of an example apparatus 700 that can facilitate prediction and/or identification of responding and/or non-responding rectal cancer patients to chemoradiation treatment and/or training a machine learning (ML) classifier to perform such prediction and/or identification, according to various embodiments discussed herein. Apparatus 700 can be configured to perform various techniques discussed herein, for example, various operations discussed in connection with sets of operations 100, 200, 300, and/or 400. Apparatus 700 can comprise one or more processors 710 and memory 720. Processor(s) 710 can, in various embodiments, comprise circuitry such as, but not limited to, one or more single-core or multi-core processors. Processor(s) 710 can include any combination of general-purpose processors and dedicated processors (e.g., graphics processors, application processors, etc.). The processor(s) can be coupled with and/or can comprise memory (e.g., of memory 720) or storage and can be configured to execute instructions stored in the memory 720 or storage to enable various apparatus, applications, or operating systems to perform operations and/or methods discussed herein. Memory 720 can be configured to store one or more image volumes (e.g., MRI, etc.) of a rectum, for example, a rectum of a patient with rectal cancer (e.g., for training and/or classification), or a healthy rectum (e.g., for construction of a rectal atlas). Each of the image(s) of the image volume can comprise a plurality of pixels or voxels, each pixel or voxel having an associated intensity. Memory 720 can be further configured to store additional data involved in performing operations discussed herein, such as for determining response to chemoradiation treatment of a rectal cancer patient and/or training a ML or DL model to determine response to chemoradiation treatment of a rectal cancer patient, as discussed in greater detail herein.

Apparatus 700 can also comprise an input/output (I/O) interface 730 (e.g., associated with one or more I/O devices), a set of circuits 750, and an interface 740 that connects the processor(s) 710, the memory 720, the I/O interface 730, and the set of circuits 750. I/O interface 730 can be configured to transfer data between memory 720, processor 710, circuits 750, and external devices, for example, a medical imaging device (e.g., MRI system or apparatus, etc.), and/or one or more remote devices for receiving inputs and/or providing outputs to a clinician, patient, etc., such as optional personalized medicine device 760.

The processor(s) 710 and/or one or more circuits of the set of circuits 750 can perform one or more acts associated with a method or set of operations discussed herein, such as set of operations 100, 200, 300, or 400. In various embodiments, different acts (e.g., different operations of a set of operations) can be performed by the same or different processor(s) 710 and/or one or more circuits of the set of circuits 750.

Apparatus 700 can optionally further comprise personalized medicine device 760. Apparatus 700 can be configured to provide the determination or prediction of response to chemoradiation treatment for a rectal cancer patient, or other data to personalized medicine device 760. Personalized medicine device 760 may be, for example, a computer assisted diagnosis (CADx) system or other type of personalized medicine device that can be used to facilitate monitoring and/or treatment of an associated medical condition. In some embodiments, processor(s) 710 and/or one or more circuits of the set of circuits 750 can be further configured to control personalized medicine device 760 to display the determination or prediction of response to chemoradiation treatment for the patient or other data on a computer monitor, a smartphone display, a tablet display, or other displays.

Examples herein can include subject matter such as an apparatus, an MRI system, a CT system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for generating system-independent quantitative perfusion measurements, according to embodiments and examples described.

In some embodiments, in addition to determining a magnitude of a deformation due to a rectal tumor, one or more orientation based deformation features may also be determined for the deformation. The one or more orientation based deformation features describe a direction of a change in a size of the deformation. By determining both a magnitude and a direction of a change in a size of a deformation, a more accurate prognosis can be made regarding a progression and/or a response to treatment of a rectal tumor.

Figure 8:
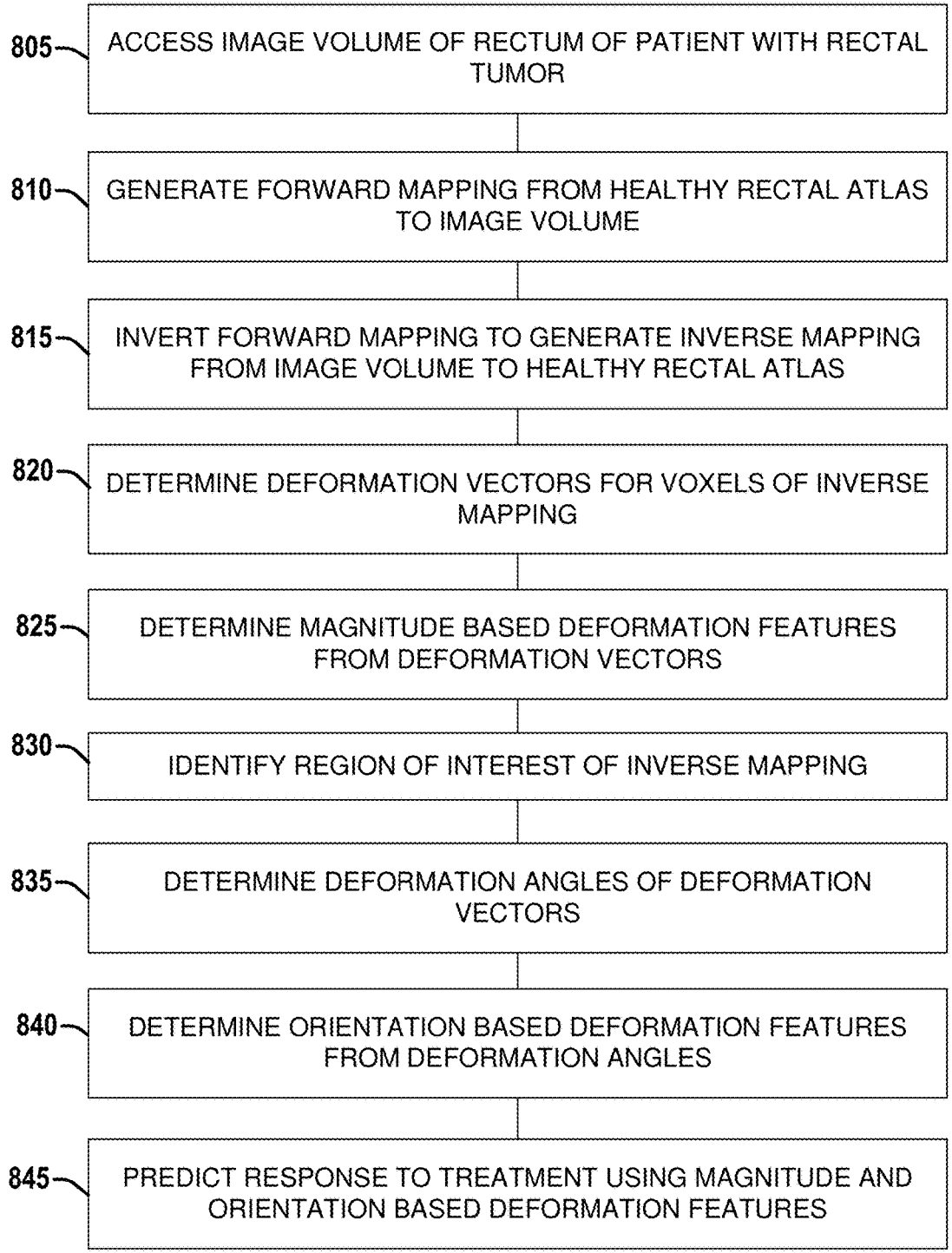
FIG. 8, illustrates a flow diagram of an example method/set of operations that can be performed by one or more processors to predict a response to chemoradiation treatment based on structural deformation features that include both a magnitude based deformation feature and an orientation based deformation feature of an imaging volume of a rectum of a patient with rectal cancer, according to various aspects discussed herein.

Referring to FIG. 8, illustrated is a flow diagram of an example method/set of operations 800 that can be performed by one or more processors to predict a response to chemoradiation treatment based on structural deformation features that include both a magnitude based deformation feature and an orientation based deformation feature of an imaging volume of a rectum of a patient with rectal cancer, according to various aspects discussed herein.

The set of operations 800 can comprise, at 805, accessing an image volume of a rectum of a patient with a rectal tumor. In some embodiments, the image volume may be obtained prior to chemoradiation treatment. In other embodiments, the image volume may be obtained after chemoradiation treatment. In some embodiments, the image volume can comprise MRI image data. In other embodiments, the image volume may comprise image data from other imaging types (e.g., CT scans, PET scans, ultrasounds, x-rays, or the like). The image volume can be obtained via a system and/or apparatus implementing the set of operations 800, or can be obtained from a separate medical imaging system. Additionally, the image volume can be accessed contemporaneously with or at any point prior to performing the set of operations 800.

The set of operations 800 can further comprise, at 810, generating a forward mapping from a healthy rectal atlas (e.g., generated according to techniques discussed herein, etc.) to the image volume via techniques discussed herein (e.g., via non-rigid registration, etc.).

The set of operations 800 can further comprise, at 815, inverting the forward mapping to generate an inverse mapping from the image volume to the healthy rectal atlas. Inverting the forward mapping allows for structural deformations in the rectal environment to be quantified with respect to the healthy rectal atlas.

The set of operations 800 can further comprise, at 820, determining a deformation vector for each voxel of an intra-wall and/or peri-wall region based on the inverse mapping (e.g., in one or more sites N consecutive slices associated with a tumor, etc.).

The set of operations 800 can further comprise, at 825, computing one or more magnitude based deformation features from the deformation vectors. The one or more magnitude based features can comprise statistical measures of the deformation vectors (e.g., from the intra-wall voxels and/or the peri-wall voxels).

The set of operations 800 can further comprise, at 830, determining a region of interest of the inverse mapping. In some embodiments, the region of interest may be a subarea of the rectum with a largest magnitude of deformation.

The set of operations 800 can further comprise, at 835, determining deformation angles from each of the deformation vectors. The deformation angles may be determined for deformation vectors within the intra-wall voxels and/or the peri-wall voxels.

The set of operations 800 can further comprise, at 840, computing one or more orientation based deformation features from the deformation angles.

The set of operations 800 can further comprise, at 845, predicting a response to chemoradiation treatment based on the one or more magnitude based deformation features and the one or more orientation based deformation features.

Figure 9:
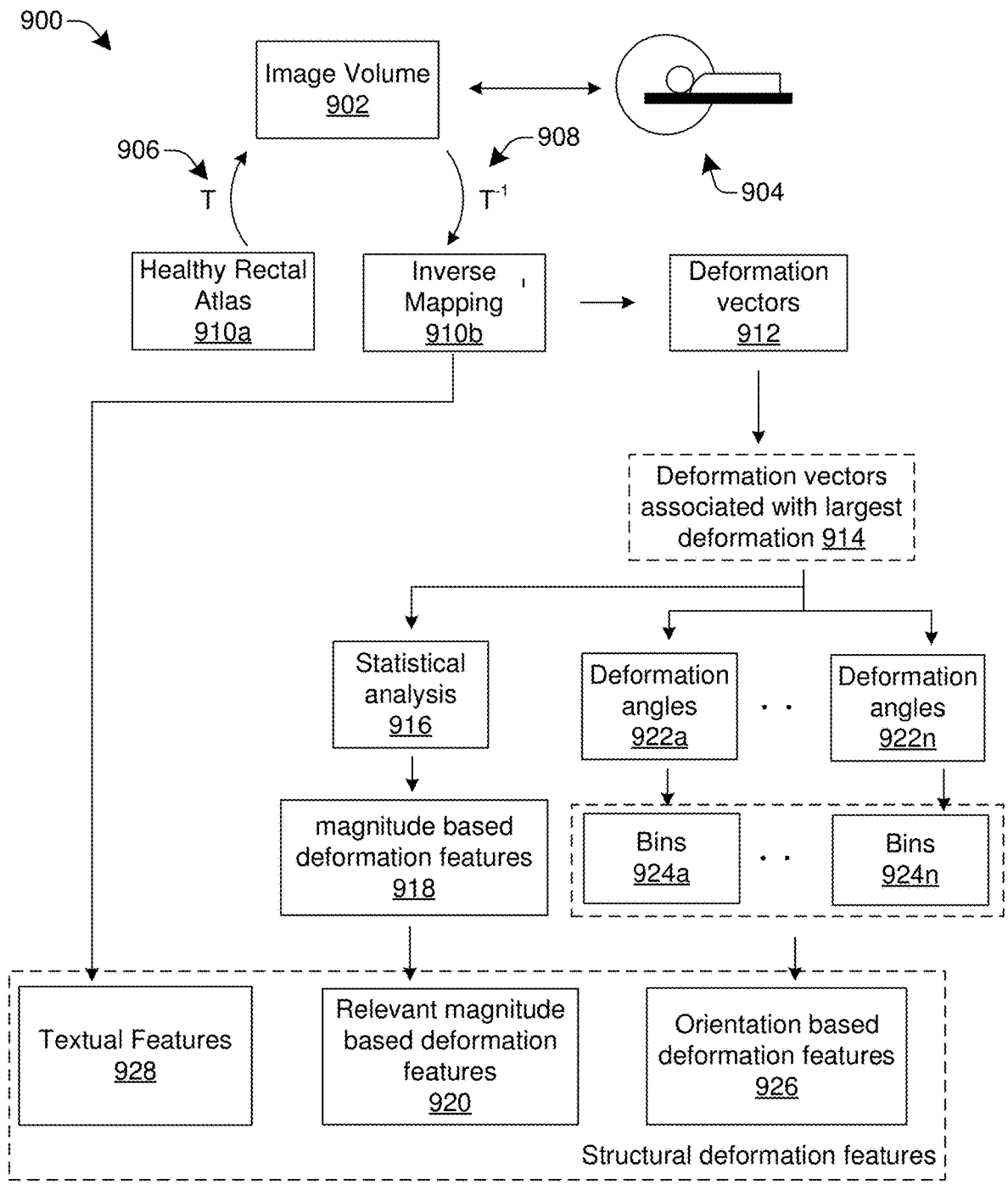
FIG. 9 illustrates a block diagram showing some additional embodiments of a method of determining a response to treatment of a patient having a rectal tumor.

FIG. 9 illustrates a block diagram 900 showing some additional embodiments of a method of determining a response to treatment of a patient having a rectal tumor. It will be appreciated that in various embodiments, the method illustrated by block diagram 900 may be implemented on circuits of an apparatus (e.g., on the circuits 750 of apparatus 700 of FIG. 7), may be stored as computer-executable instructions on a computer readable medium, or may be performed as a method.

As shown in block diagram 900, an image volume 902 of a rectum of a patient having a rectal tumor is obtained. The image volume 902 comprises one or more images of the rectum of the patient having the rectal tumor. In some embodiments the image volume 902 may comprise one or more pre-treatment images taken from the patient before the patient receives chemoradiation treatment. In other embodiments, the image volume 902 may comprise one or more post-treatment images taken from the patient after the patient receives chemoradiation treatment. In some embodiments, the image volume may be obtained from data received from a medical imaging device 904 (e.g., a MRI scanner, a PET scanner, a CT scanner, or the like).

A healthy rectal atlas 910a is provided. The healthy rectal atlas 910a may comprise image data from a plurality of images of health rectums. The healthy rectal atlas 910a is non-rigidly registered to each rectal wall of the image volume 902 using a normalized mutual information-based similarity measure. This non-rigid alignment provides a forward transformation, T that maps the healthy rectal atlas 910a to the image volume 902. An inverse transformation, $T^{-1}$, is used to map the image volume 902 back to an inverse mapping 910b. The inverse mapping process determines structural deformations hypothesized to occur as a result of tumor-related growth or shrinkage of the rectal wall.

Deformation vectors 912 are computed from the inverse mapping 910b. The deformation vectors 912 are vectors that indicate a change in position of a point on a rectum in the inverse mapping 910b. In some embodiments, the deformation vectors 912 may be determined for each voxel of the inverse mapping 910b. In some embodiments, deformation vectors associated with an area of interest 914 of the inverse mapping 910b are identified. The deformation vectors associated with an area of interest 914 may comprise deformation vectors within the area having a largest deformation (e.g., a largest magnitude of deformation) within the rectal wall of the inverse mapping 910b. In some embodiments, the area having a largest deformation within the rectal wall may be identified by clustering deformation magnitude values via a Markov random field (MRF)-based technique.

One or more magnitude based deformation features 918 and one or more orientation based deformation features 926 are determined from the deformation vectors associated with the area of interest 914. For example, the one or more magnitude based deformation features 918 may comprise 4 magnitude based deformation features and the one or more orientation based deformation features 926 may comprise 5 orientation based deformation features.

In some embodiments, the one or more magnitude based deformation features 918 may be calculated by performing statistical analysis 916 on the deformation vectors associated with the area of interest 914. In such embodiments, the one or more magnitude based deformation features 918 may be statistical features of magnitudes of the deformation vectors associated with the area of interest 914. In some embodiments, the statistical features may comprise median, variance, kurtosis, and/or skewness of the magnitudes of the deformation vectors associated with the area of interest 914.

From the one or more magnitude based deformation features 918 a subset of relevant magnitude based deformation features 920 may be selected to improve prognosis of tumor regression. The subset may selected to determine statistical measurements that are most relevant to prognosis to tumor regression. In some embodiments, the relevant magnitude based deformation features 920 may be associated with pathologic tumor stage regression (e.g., based on an evaluation with excised specimens). In some embodiments, the relevant magnitude based deformation features 920 may be identified via cross-validation on a training subset. In some embodiments, the training set may comprise a first plurality of patients (e.g., 40 patients from a first medical center, 48 patients from two different medical centers, etc.). In some embodiments, the first the training set may be evaluated using linear analysis. In some embodiment, a hold-out validation may be performed using a first group of patients from a first medical site as a training set and a second group of patients from a second medical site as a test set.

In some embodiments, the orientation based deformation features 926 may be determined by computing deformation angles 922a-922n for each deformation vector associated with the area of interest 914. In some embodiments, the deformation angles 922a-922n may be determined with respect to a lumen centroid of the rectum. By determining deformation angles 922a-922n with respect to the lumen centroid of the rectum, the deformation angles 922a-922n can determine movement of a deformation inward (e.g., if an angle is less than 90°) or outward (e.g., if an angle is greater than) 90° from the lumen along different sides of the rectal wall surrounding the lumen. In some embodiments, the deformation angles 922a-922n may be determined with respect to the lumen centroid based on a geometric transformation (e.g., a $\cos^{-1}$ transformation). In some embodiments, the deformation angles 922a-922n may be quantized into a plurality of bins 924a-924n respectively corresponding to a deformation based orientation feature. The plurality of bins may represent different growth categories (e.g., different gradations and/or directions of growth with respect to the lumen centroid). For example, a first plurality of deformation angles 922a may be placed within a first bin 924a corresponding to a first range of angles that represent tumor-related growth and a second plurality of deformation angles 922n may be placed within a second bin 924b corresponding to a second range of angles that represent tumor related shrinkage.

In some embodiments, the plurality of bins 924a-924n may comprise 5 bins (e.g., a first bin having a range of between 0° and 20°, a second bin having a range of between 20° and 80°, a third bin having a range of between 80° and 100°, a fourth bin having a range of between 100° and 160°, a fifth bin having a range of between 160° and 180°). In such embodiments, the plurality of bins may result in 5 deformation orientation features representing inward and outward deformations of a rectal wall. For example, the first bin may represent strong inward growth toward the lumen centroid, the second bin may represent mild inward growth toward the lumen centroid, the third bin may represent substantially stagnant growth toward the lumen centroid, the fourth bin may represent mild outward growth away from the lumen centroid, and the fifth bin may represent strong outward growth away from the lumen centroid.

In some additional embodiments, one or more texture features 928 may be calculated for the intra-wall region and/or the peri-wall region. The one or more texture features 928 may be calculated from the inverse mapping 910b based on features of the images (e.g., based on brightness of voxels within the images).

In some embodiment, the relevant magnitude based deformation features 920 and the one or more orientation based deformation features 926 may distinguish low pathologic tumor stages (e.g., ypT0-ypT2 patients) and high pathologic tumor stages (e.g., ypT3-ypT4 patients) after neoadjuvant chemoradiation therapy (nCRT). In some embodiments, the relevant magnitude based deformation features 920 and the one or more orientation based deformation features 926 may indicate larger deformations contracting from the rectal wall to the lumen for ypT3-ypT4 patients, and shorter deformations oriented outward from the rectal wall and away from the lumen for ypT0-ypT2 patients.

In one example, the relevant magnitude based deformation features 920 provided a prognosis of rectal tumor progression with in an area under curve (AUC) of 0.79 in a training set, and an AUC of 0.70 on hold-out validation. In one example, a combination of the relevant magnitude based deformation features 920, the one or more orientation based deformation features 926, and the texture features 928 provided a prognosis of a rectal tumor progression with an AUC of 0.86 in the training set, and an AUC of 0.77 on hold-out validation. Therefore, based on the above AUCs the one or more orientation based deformation features 926 of the rectal wall are highly relevant for discriminating patients with low and high tumor stage after chemoradiation, likely capturing implicit effects of residual tumor expanding or contracting the rectum.

Figure 10A:
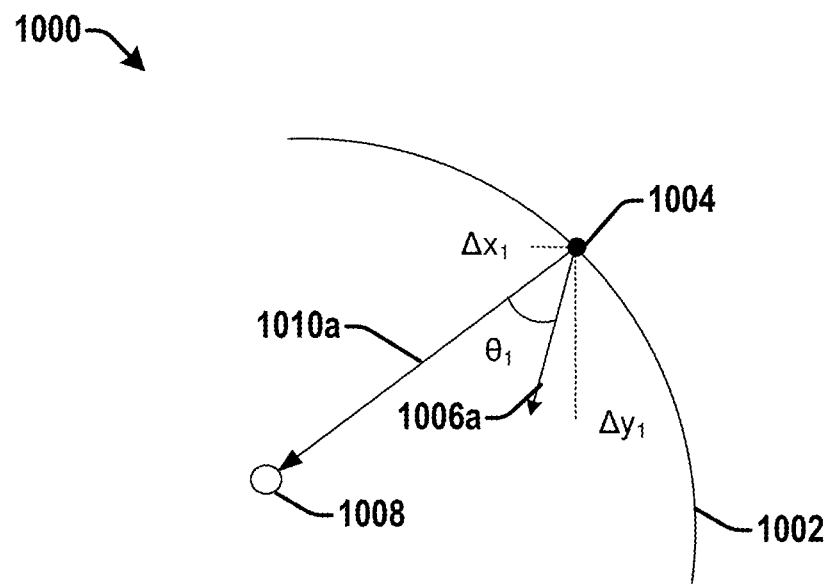
FIGS. 10A-10B illustrate schematic diagrams showing an exemplary method of calculating deformation angles from a deformation vector representing a deformation of a rectal wall.
Figure 10B:
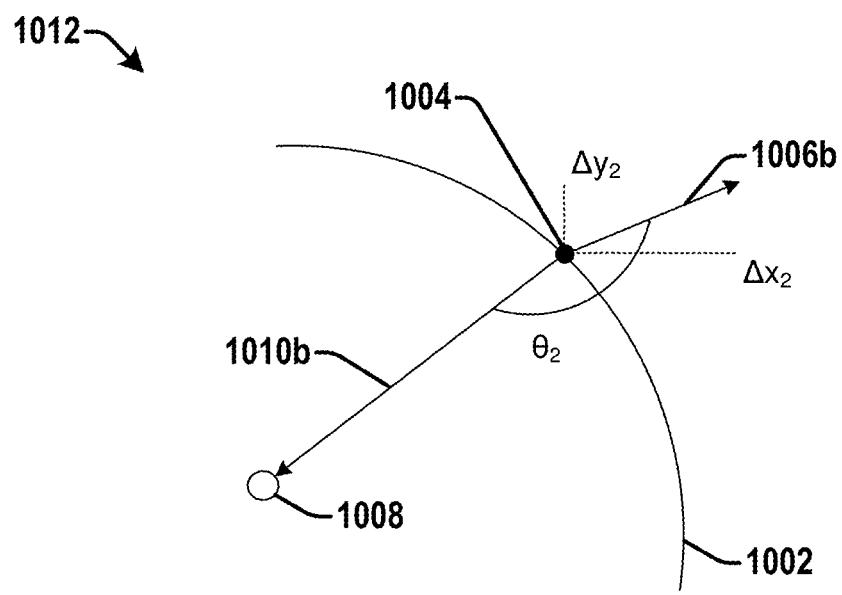

FIGS. 10A-10B illustrate schematic diagrams showing an exemplary method of calculating deformation angles from a deformation vector representing a deformation of a rectal wall. In the schematic diagrams of FIGS. 10A-10B deformation angles less than 90° denote an inward deformation (e.g., a deformation towards a lumen centroid) while deformation angles greater than 90° denote an outward deformation (e.g., a deformation away from a lumen centroid). However, it will be appreciated that in other embodiments other deformation angle ranges may be used to denote inward and outward deformations.

FIG. 10A illustrates a schematic diagram 1000 showing a first deformation vector 1006a associated with an inward deformation of a rectal wall of a rectum.

The first deformation vector 1006a describes a hypothesized change in position of a point 1004 along a rectal wall 1002 of a rectum. The first deformation vector 1006a extends for a first distance $\Delta x_1$ in an x-direction and for a first distance $\Delta y_1$ in a y-direction of a Cartesian coordinate system centered upon the point 1004. A first additional vector 1010a extends from the point 1004 to a lumen centroid 1008 of the rectum. A first deformation angle θ1 of the first deformation vector 1006a is determined as an $\cos^{-1}$ of a dot product of the first deformation vector 1006a and the first additional vector 1010a divided by a dot product of an absolute value of the first deformation vector 1006a and an absolute value the first additional vector 1010a (e.g., $$\theta_1 = \cos^{-1} \frac{a_1 \cdot b_1}{|a_1| \cdot |b_1|},$$

wherein $a_1$ is the first deformation vector 1006a and $b_1$ is the first additional vector 1010a). For example, if the first deformation vector 1006a is $-5i-10j$ and the first additional vector 1010a is $-20i-15j$, the first deformation angle $\theta_1$ of the first deformation vector 1006a would be $$\cos^{-1} \frac{100+150}{\sqrt{125 \times 625}} = 26.1°.$$

Since the first deformation angle $\theta_1$ is less than 90° it denotes that the deformation at the point 1004 is an inward deformation (e.g., a deformation towards the lumen centroid 1008).

FIG. 10B illustrates a schematic diagram 1012 showing a deformation vector associated with an outward deformation of a rectal wall of a rectum.

The second deformation vector 1006b is a vector describing a hypothesized change in position of a point 1004 along a rectal wall 1002 of a rectum. The second deformation vector 1006b extends for a second distance $\Delta x_2$ in an x-direction and for a second distance $\Delta y_2$ in a y-direction of a Cartesian coordinate system centered upon the point 1004. A second additional vector 1010b extends from the point 1004 to a lumen centroid 1008. A second deformation angle $\theta_2$ of the second deformation vector 1006b is determined as an $\cos^{-1}$ of a dot product of the second deformation vector 1006b and the second additional vector 1010b divided by a dot product of an absolute value of second deformation vector 1006b and an absolute value the second additional vector 1010b $$\text{(e.g., } \theta_2 = \cos^{-1} \frac{a_2 \cdot b_2}{|a_2| \cdot |b_2|},$$

wherein $a_2$ is the second deformation vector 1006b and $b_2$ is the second additional vector 1010b). For example, if the second deformation vector 1006b is 10i+5j and the second additional vector 1010b is −20i-15j, the second deformation angle $\theta_2$ of the second deformation vector 1006b would be $$\cos^{-1} \frac{-200 - 75}{\sqrt{125 \times 625}} = 169.1°.$$

Since the second deformation angle $\theta_2$ is greater than 90° it denotes that the deformation at the point 1004 is an outward deformation (e.g., a deformation away from the lumen centroid 1008).

Figure 11A:
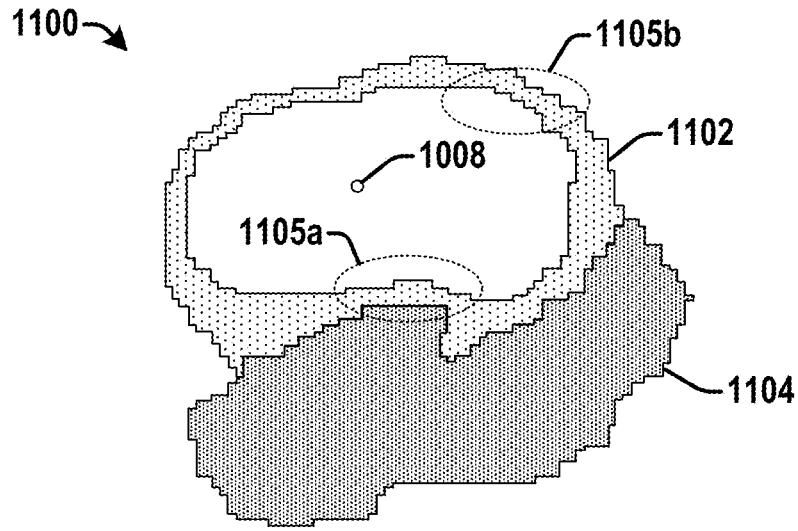
FIGS. 11A-11C illustrate exemplary cross-sectional views of a rectal region showing an example calculation of orientation based deformation features.
Figure 11B:
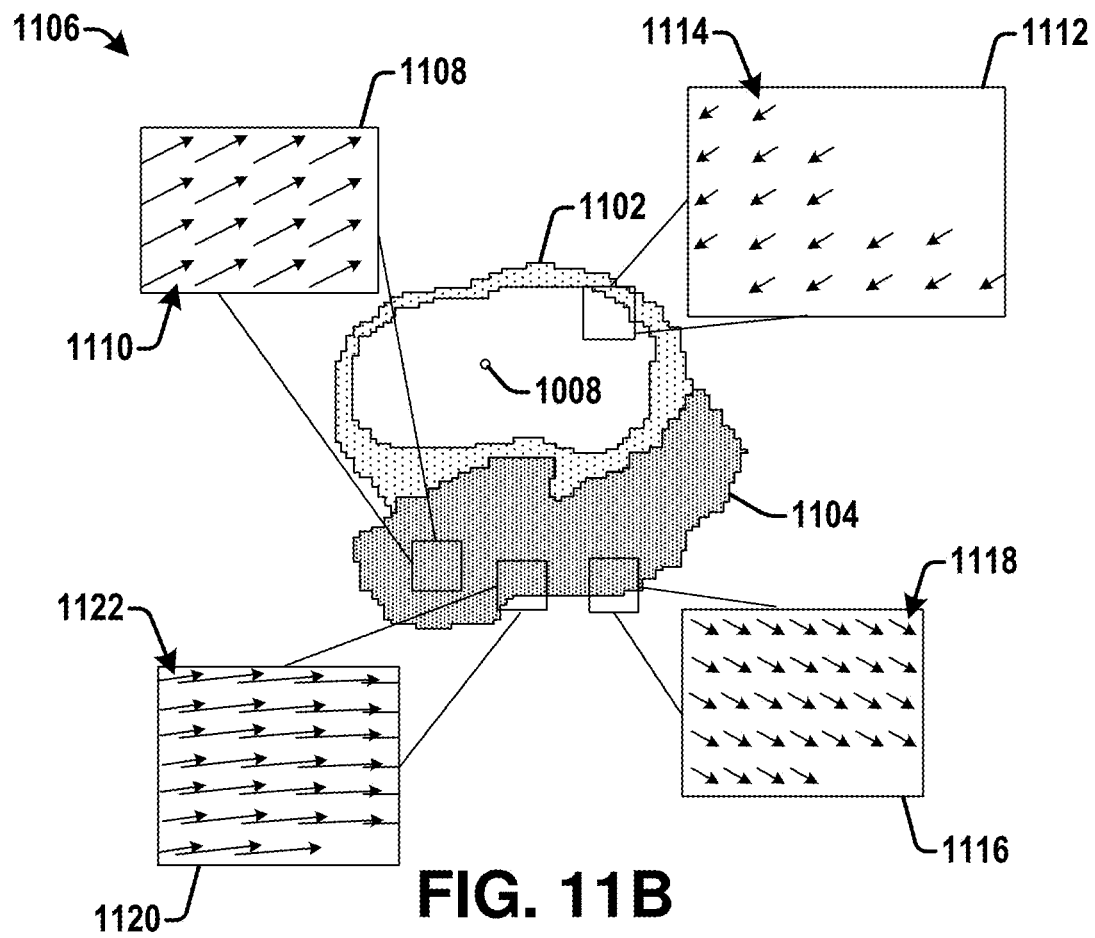
Figure 11C:
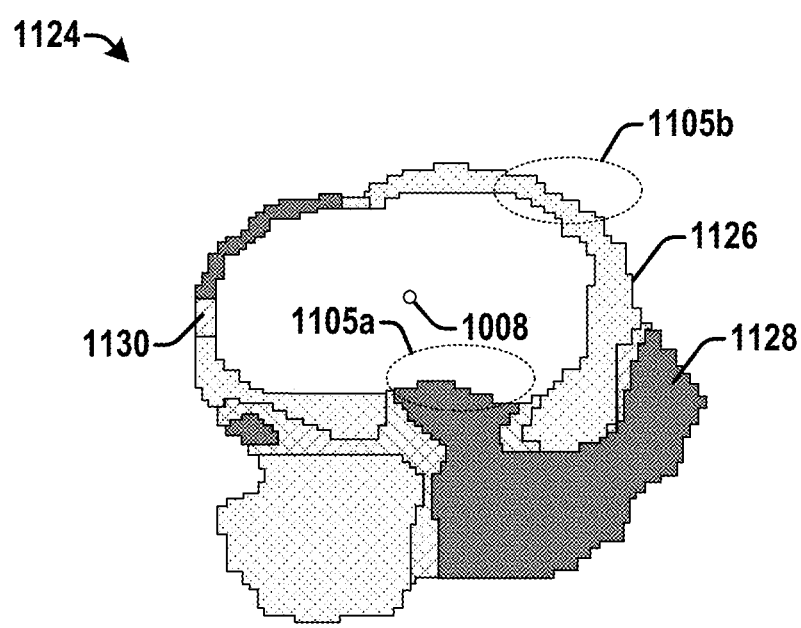

FIGS. 11A-11C illustrate exemplary cross-sectional views of a rectal region showing an example calculation of orientation based deformation features.

As shown in cross-sectional view 1100 of FIG. 11A, a rectal region comprises a rectal wall region 1102 and a tumor region 1104. The tumor region 1104 abuts the rectal wall region 1102. The rectal wall region 1102 may comprise a plurality of deformations 1105a-1105b. In some embodiments, one or more of the plurality of deformations 1105a-1105b may be the result of the tumor region 1104 pushing on the rectal wall region 1102. The rectal wall region 1102 surrounds a lumen that is centered upon a lumen centroid 1008.

Deformation vectors are determined for voxels extending over the rectal wall region 1102 and the tumor region 1104 (e.g., for all voxels extending over an entirety of the rectal wall region 1102 and the tumor region 1104). Cross-sectional view 1106 illustrates deformation vectors taken from a plurality of different areas 1108, 1112, 1116, and 1120 within of the rectal wall region 1102 and the tumor region 1104. For example, in a first area 1108 a first plurality of deformation vectors 1110 are determined, in a second area 1112 a second plurality of deformation vectors 1114 are determined, in a third area 1116 a third plurality of deformation vectors 1118 are determined, and in a fourth area 1120 a fourth plurality of deformation vectors 1122 are determined. The deformation vectors 1110, 1114, 1118, and 1122 in the plurality of different areas 1108, 1112, 1116, and 1120 have different magnitudes and different orientations.

Deformation angles may be determined for deformation vectors in one or more of the different areas 1108, 1112, 1116, and 1120. The deformation angles may be categorized into different bins corresponding to different orientation based deformation features. For example, FIG. 11C illustrates a cross-sectional view 1124 having a first area 1126 corresponding to deformation angles that fall within a first bin, a second area 1128 corresponding to deformation angles that fall within a second bin, and a third area 1130 corresponding to deformation angles that fall within a third bin. The deformation angles within the first area 1126 (e.g., deformation angles falling into the first bin) indicate a deformation within the first area 1126 is growing. The deformation angles within the second area 1128 (e.g., deformation angles falling into the second bin) indicate a deformation within the second area 1128 is substantially stagnant (e.g., not significantly increasing or decreasing). The deformation angles within the third area 1130 (e.g., deformation angles falling into the third bin) indicate a deformation within the third area 1130 is shrinking.

The magnitudes of the deformation vectors 1110, 1114, 1118, and 1122 may also be determined and used to identify a magnitude of a change in a deformation within the rectal wall region 1102 and the tumor region 1104. In some embodiments, a largest deformation may be identified from the magnitudes. In some embodiments, prognosis of changes in the rectal wall may be limited to the largest deformation. For example, in some embodiments, the magnitudes of the deformation vectors 1110, 1114, 1118, and 1122 may indicate that deformation 1105a is a largest deformation and prognosis of changes in the rectal wall may be limited to the bins associated with deformation 1105a (e.g., only deformation based orientation and magnitude based features within deformation 1105a are considered in providing a prognosis of a rectal tumor progression).

Therefore, from the orientation based deformation features, a direction of a growth and/or a shrinkage of a deformation due to a rectal tumor may be determined. Furthermore, from the magnitude based deformation features a size of the growth and/or shrinkage of the deformation can also be determined, thereby giving an accurate prognosis of changes in the rectal tumor.

Example 1 is a non-transitory computer-readable medium storing computer-executable instructions that, when executed, cause a processor to perform operations, comprising: accessing an image volume of a rectum comprising a rectal tumor; generating a forward mapping based on non-rigidly registering a healthy rectal atlas to the image volume; inverting the forward mapping to generate an inverse mapping from the image volume to the healthy rectal atlas; determining, based on the inverse mapping, a plurality of deformation vectors associated with a deformation within a rectal wall of the rectum; computing magnitude based deformation features from the plurality of deformation vectors; computing orientation based deformation features from the plurality of deformation vectors; and utilizing one or more of the magnitude based deformation features and one or more of the orientation based deformation features to determine a response of a patient to a chemoradiation treatment.

Example 2 comprises the subject matter of any variation of any of example(s) 1, wherein the image volume is obtained prior to the chemoradiation treatment.

Example 3 comprises the subject matter of any variation of any of example(s) 1-2, wherein the image volume is obtained after the chemoradiation treatment.

Example 4 comprises the subject matter of any variation of any of example(s) 1-3, wherein the rectal wall comprises a plurality of deformations and the deformation is a largest deformation of the plurality of deformations.

Example 5 comprises the subject matter of any variation of any of example(s) 4, wherein the operations further comprise determining a set of relevant magnitude based deformation features from the magnitude based deformation features, the set of relevant magnitude based deformation features being less than the magnitude based deformation features; and utilizing the set of relevant magnitude based deformation features and the one or more of the orientation based deformation features to determine a prognosis associated with tumor regression.

Example 6 comprises the subject matter of any variation of any of example(s) 1-5, wherein the operations further comprise determining a plurality of deformation angles corresponding to the plurality of deformation vectors; placing the plurality of deformation angles into a plurality of bins; and determining an orientation based deformation feature of the orientation based deformation features based on one or more of the plurality of deformation angles within one the plurality of bins.

Example 7 comprises the subject matter of any variation of any of example(s) 6, wherein the operations further comprise determining the deformation angles with respect to a lumen centroid of the rectum.

Example 8 comprises the subject matter of any variation of any of example(s) 1-7, wherein the plurality of bins respectively correspond to different ranges of angles between 0° and 180°.

Example 9 comprises the subject matter of any variation of any of example(s) 1-8, wherein the plurality of bins comprise a first bin with one or more first deformation angles indicating the deformation is increasing in size and a second bin with one or more second deformation angles indicating that the deformation is decreasing in size.

Example 10 comprises the subject matter of any variation of any of example(s) 1-9, wherein the orientation based deformation features describe a direction of a change in size of the rectal tumor.

Example 11 is a non-transitory computer-readable medium storing computer-executable instructions that, when executed, cause a processor to perform operations, comprising: accessing an image volume of a rectum having a rectal wall, wherein the rectal wall comprises a plurality of deformations; generating a forward mapping based on non-rigidly registering a healthy rectal atlas to the image volume; inverting the forward mapping to generate an inverse mapping from the image volume to the healthy rectal atlas; determining a plurality of deformation vectors for a plurality of voxels within the inverse mapping, the plurality of deformation vectors describing a deformation within the rectal wall that is a largest deformation of the plurality of deformations; computing magnitude based deformation features and orientation based deformation features from the plurality of deformation vectors; and utilizing one or more of the magnitude based deformation features and one or more of the orientation based deformation features to determine a magnitude and a direction of a change in the deformation.

Example 12 comprises the subject matter of any variation of any of example(s) 11, wherein the operations further comprise determining a set of relevant magnitude based deformation features from the magnitude based deformation features, the set of relevant magnitude based deformation features being less than the magnitude based deformation features; and utilizing the set of relevant magnitude based deformation features and the one or more of the orientation based deformation features to determine a prognosis associated with tumor regression.

Example 13 comprises the subject matter of any variation of any of example(s) 11-12, wherein the operations further comprise utilizing one or more of the magnitude based deformation features and one or more of the orientation based deformation features to determine a response of a patient to chemoradiation treatment.

Example 14 comprises the subject matter of any variation of any of example(s) 11-13, wherein the operations further comprise determining a plurality of deformation angles corresponding to the plurality of deformation vectors; placing the plurality of deformation angles into a plurality of bins; and determining an orientation based deformation feature of the orientation based deformation features based on one or more of the plurality of deformation angles within one the plurality of bins.

Example 15 comprises the subject matter of any variation of any of example(s) 14, wherein the operations further comprise determining the deformation angles with respect to a lumen centroid of the rectum.

Example 16 comprises the subject matter of any variation of any of example(s) 11-15, wherein the magnitude based deformation features comprise one or more of a median, variance, kurtosis, and skewness.

Example 17 comprises the subject matter of any variation of any of example(s) 11-16, wherein the image volume is a Magnetic Resonance Imaging (MRI) image volume.

Example 18 is a method of performing a prognosis of medical treatment, comprising accessing an image volume of a rectum having a rectal wall, wherein the rectal wall comprises a plurality of deformations; generating a forward mapping based on non-rigidly registering a healthy rectal atlas to the image volume; inverting the forward mapping to generate an inverse mapping from the image volume to the healthy rectal atlas; determining, based on the inverse mapping, a plurality of deformation vectors describing a deformation within the rectal wall, wherein the deformation is a largest deformation of the plurality of deformations; computing magnitude based deformation features and orientation based deformation features from the plurality of deformation vectors; and utilizing one or more of the magnitude based deformation features and one or more of the orientation based deformation features to determine a magnitude and direction of a change in the deformation due to a chemotherapy treatment Example 19 comprises the subject matter of any variation of any of example(s) 18, wherein the method further comprises obtaining the image volume prior to the chemotherapy treatment.

Example 20 comprises the subject matter of any variation of any of example(s) 18, wherein the method further comprises obtaining the image volume after the chemotherapy treatment.

Example 21 comprises an apparatus comprising means for executing any of the described operations of examples 1-20.

Example 22 comprises a machine readable medium that stores instructions for execution by a processor to perform any of the described operations of examples 1-20.

Example 23 comprises an apparatus comprising: a memory; and one or more processors configured to: perform any of the described operations of examples 1-20.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:
    accessing an image volume of a rectum comprising a rectal tumor;
    generating a forward mapping based on non-rigidly registering a healthy rectal atlas to the image volume;
    inverting the forward mapping to generate an inverse mapping from the image volume to the healthy rectal atlas;
    determining, based on the inverse mapping, a plurality of deformation vectors associated with a deformation within a rectal wall of the rectum;
    computing magnitude based deformation features from the plurality of deformation vectors;
    computing orientation based deformation features from the plurality of deformation vectors; and
    utilizing one or more of the magnitude based deformation features and one or more of the orientation based deformation features to determine a response of a patient to a chemoradiation treatment.

2. The non-transitory computer-readable medium of claim 1, wherein the image volume is obtained prior to the chemoradiation treatment.

3. The non-transitory computer-readable medium of claim 1, wherein the image volume is obtained after the chemoradiation treatment.

4. The non-transitory computer-readable medium of claim 1, wherein the rectal wall comprises a plurality of deformations and the deformation is a largest deformation of the plurality of deformations.

5. The non-transitory computer-readable medium of claim 1, further comprising:
    determining a set of relevant magnitude based deformation features from the magnitude based deformation features, the set of relevant magnitude based deformation features being less than the magnitude based deformation features; and
    utilizing the set of relevant magnitude based deformation features and the one or more of the orientation based deformation features to determine a prognosis associated with tumor regression.

6. The non-transitory computer-readable medium of claim 1, further comprising:
    determining a plurality of deformation angles corresponding to the plurality of deformation vectors;
    placing the plurality of deformation angles into a plurality of bins; and
    determining an orientation based deformation feature of the orientation based deformation features based on one or more of the plurality of deformation angles within one the plurality of bins.

7. The non-transitory computer-readable medium of claim 6, further comprising:
    determining the deformation angles with respect to a lumen centroid of the rectum.

8. The non-transitory computer-readable medium of claim 6, wherein the plurality of bins respectively correspond to different ranges of angles between 0° and 180°.

9. The non-transitory computer-readable medium of claim 6, wherein the plurality of bins comprise a first bin with one or more first deformation angles indicating the deformation is increasing in size and a second bin with one or more second deformation angles indicating that the deformation is decreasing in size.

10. The non-transitory computer-readable medium of claim 1, wherein the orientation based deformation features describe a direction of a change in size of the rectal tumor.

11. A non-transitory computer-readable medium storing computer-executable instructions that, when executed, cause a processor to perform operations, comprising:
- accessing an image volume of a rectum having a rectal wall, wherein the rectal wall comprises a plurality of deformations;
- generating a forward mapping based on non-rigidly registering a healthy rectal atlas to the image volume;
- inverting the forward mapping to generate an inverse mapping from the image volume to the healthy rectal atlas;
- determining a plurality of deformation vectors for a plurality of voxels within the inverse mapping, the plurality of deformation vectors describing a deformation within the rectal wall that is a largest deformation of the plurality of deformations;
- computing magnitude based deformation features and orientation based deformation features from the plurality of deformation vectors; and
- utilizing one or more of the magnitude based deformation features and one or more of the orientation based deformation features to determine a magnitude and a direction of a change in the deformation.

12. The non-transitory computer-readable medium of claim 11, further comprising:
- determining a set of relevant magnitude based deformation features from the magnitude based deformation features, the set of relevant magnitude based deformation features being less than the magnitude based deformation features; and
- utilizing the set of relevant magnitude based deformation features and the one or more of the orientation based deformation features to determine a prognosis associated with tumor regression.

13. The non-transitory computer-readable medium of claim 11, further comprising:
- utilizing one or more of the magnitude based deformation features and one or more of the orientation based deformation features to determine a response of a patient to chemoradiation treatment.

14. The non-transitory computer-readable medium of claim 11, further comprising:
- determining a plurality of deformation angles corresponding to the plurality of deformation vectors;
- placing the plurality of deformation angles into a plurality of bins; and
- determining an orientation based deformation feature of the orientation based deformation features based on one or more of the plurality of deformation angles within one the plurality of bins.

15. The non-transitory computer-readable medium of claim 14, further comprising:
- determining the deformation angles with respect to a lumen centroid of the rectum.

16. The non-transitory computer-readable medium of claim 11, wherein the magnitude based deformation features comprise one or more of a median, variance, kurtosis, and skewness.

17. The non-transitory computer-readable medium of claim 11, wherein the image volume is a Magnetic Resonance Imaging (MRI) image volume.

18. A method of performing a prognosis of medical treatment, comprising:
- accessing an image volume of a rectum having a rectal wall, wherein the rectal wall comprises a plurality of deformations;
- generating a forward mapping based on non-rigidly registering a healthy rectal atlas to the image volume;
- inverting the forward mapping to generate an inverse mapping from the image volume to the healthy rectal atlas;
- determining, based on the inverse mapping, a plurality of deformation vectors describing a deformation within the rectal wall, wherein the deformation is a largest deformation of the plurality of deformations;
- computing magnitude based deformation features and orientation based deformation features from the plurality of deformation vectors; and
- utilizing one or more of the magnitude based deformation features and one or more of the orientation based deformation features to determine a magnitude and direction of a change in the deformation due to a chemotherapy treatment.

19. The method of claim 18, further comprising:
obtaining the image volume prior to the chemotherapy treatment.

20. The method of claim 18, further comprising:
obtaining the image volume after the chemotherapy treatment.

* * * * *